_(12)_ United States Patent
Kim et al.

(10) Patent No.: US 10,032,986 B2
(45) Date of Patent: Jul. 24, 2018

(54) POLYCYCLIC COMPOUND AND ORGANIC LIGHT EMITTING DEVICE INCLUDING THE SAME

(71) Applicant: LG CHEM, LTD., Seoul (KR)

(72) Inventors: Jin Joo Kim, Daejeon (KR); Sung Kil Hong, Daejeon (KR); Yongbum Cha, Daejeon (KR)

(73) Assignee: LG CHEM, LTD., Seoul (KR)

( * ) Notice: Subject to any disclaimer, the term of this patent is extended or adjusted under 35 U.S.C. 154(b) by 304 days.

(21) Appl. No.: 14/861,339

(22) Filed: Sep. 22, 2015

(65) Prior Publication Data

US 2016/0087216 A1    Mar. 24, 2016

(30) Foreign Application Priority Data

Sep. 23, 2014  (KR) ........................ 10-2014-0127112

(51) Int. Cl.

| | | |
|---|---|---|
| *H01L 51/00* | (2006.01) | |
| *C07D 213/16* | (2006.01) | |
| *C07D 213/57* | (2006.01) | |
| *C07D 235/30* | (2006.01) | |
| *C07C 255/52* | (2006.01) | |
| *C07C 255/50* | (2006.01) | |
| *C07D 235/08* | (2006.01) | |
| *C09K 11/06* | (2006.01) | |
| *H01L 51/50* | (2006.01) | |

(52) U.S. Cl.
CPC ........ *H01L 51/0055* (2013.01); *C07C 255/50* (2013.01); *C07C 255/52* (2013.01); *C07D 213/16* (2013.01); *C07D 213/57* (2013.01); *C07D 235/08* (2013.01); *C07D 235/30* (2013.01); *C09K 11/06* (2013.01); *H01L 51/0058* (2013.01); *H01L 51/0072* (2013.01); *H01L 51/0077* (2013.01); *H01L 51/5092* (2013.01)

(58) Field of Classification Search
CPC ... C07C 255/50; C07C 255/52; C07D 213/16; C07D 213/57; C07D 235/08; C07D 235/30; H01L 51/0055; H01L 51/0058; H01L 51/0072; H01L 51/0077; H01L 51/5092; C09K 11/06
See application file for complete search history.

(56) References Cited

U.S. PATENT DOCUMENTS

| | | | | |
|---|---|---|---|---|
| 2004/0076853 | A1* | 4/2004 | Jarikov | C09K 11/06 428/690 |
| 2010/0013381 | A1* | 1/2010 | Stoessel | C07C 13/62 313/504 |
| 2011/0108821 | A1* | 5/2011 | Kaiser | C07C 13/62 257/40 |
| 2014/0158859 | A1* | 6/2014 | Fukuzaki | H01L 51/0056 250/200 |

FOREIGN PATENT DOCUMENTS

| | | |
|---|---|---|
| KR | 20000051826 A | 8/2000 |
| KR | 10-2016-0032521 A | 3/2016 |
| WO | 03/012890 A2 | 2/2003 |
| WO | WO 2013/024693 A1 * | 2/2013 |

OTHER PUBLICATIONS

Polycyclic Aromatic Compounds, vol. 24, Issue 4-5, (2004), pp. 271-278.*

* cited by examiner

*Primary Examiner* — Dawn Garrett
(74) *Attorney, Agent, or Firm* — Dentons US LLP

(57) ABSTRACT

The present specification provides a polycyclic compound and an organic light emitting device including the same.

10 Claims, 1 Drawing Sheet

[Figure 1]
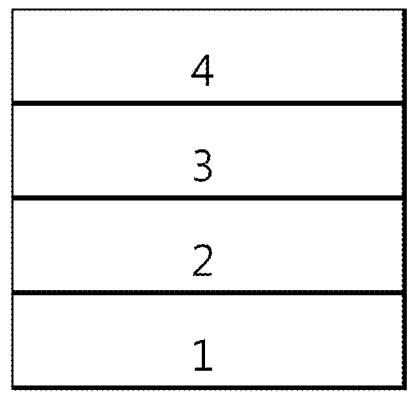
[Figure 2]
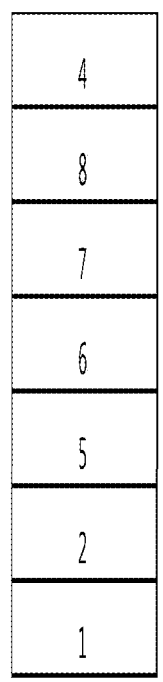

POLYCYCLIC COMPOUND AND ORGANIC LIGHT EMITTING DEVICE INCLUDING THE SAME

FIELD OF THE INVENTION

This application claims priority to and the benefits of Korean Patent Application No. 10-2014-0127112, filed with the Korean Intellectual Property Office on Sep. 23, 2014, the entire contents of which are incorporated herein by reference.

The present specification relates to a polycyclic compound and an organic light emitting device including the same.

BACKGROUND OF THE INVENTION

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

Korean Patent Application Laid-Open Publication No. 2000-0051826

SUMMARY OF THE INVENTION

The present specification describes a novel polycyclic compound and an organic light emitting device including the same.

One embodiment of the present specification provides a compound represented by the following Chemical Formula 1:

[Chemical Formula 1]

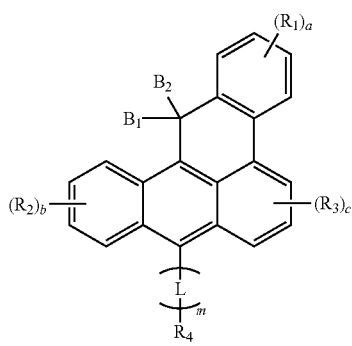

In Chemical Formula 1, $R_1$ to $R_4$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or a substituted or unsubstituted heterocring, $B_1$ and $B_2$ are the same as or different from each other, and each independently a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, L is a direct bond; a substituted or unsubstituted arylene group; or a substituted or unsubstituted heteroarylene group, m is an integer of 0 to 5, a and b are the same as or different from each other, and each independently an integer of 0 to 4, c is an integer of 0 to 3, when a is two or greater, $R_1$s are the same as or different from each other, when b is two or greater, $R_2$s are the same as or different from each other, when c is two or greater, $R_3$s are the same as or different from each other, and when m is two or greater, Ls are the same as or different from each other.

In addition, one embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

BRIEF DESCRIPTION OF THE DRAWINGS

The objects and qualities of the present invention will become apparent from the following description of embodiments given in conjunction with the accompanying drawings, in which:

FIG. 1 is a diagram showing an example of an organic light emitting device formed with a substrate (1), an anode (2), a light emitting layer (3) and a cathode (4); and FIG. 2 is a diagram showing an example of an organic light emitting device formed with a substrate (1), an anode (2), a hole injection layer (5), a hole transfer layer (6), a light emitting layer (7), an electron transfer layer (8) and a cathode (4).

1: Substrate
2: Anode

3: Light Emitting Layer
4: Cathode
5: Hole Injection Layer
6: Hole Transfer Layer
7: Light Emitting Layer
8: Electron Transfer Layer

DETAILED DESCRIPTION OF THE EMBODIMENTS

Hereinafter, the present specification will be described in more detail.

One embodiment of the present specification provides a compound of Chemical Formula 1 represented by the above-mentioned Chemical Formula 1.

Examples of the substituents are described below, however, the substituents are not limited thereto.

The term "substituted or unsubstituted" in the present specification means being substituted with one or more substituents selected from the group consisting of deuterium; a halogen group; a nitrile group; a nitro group; an amino group; an alkyl group; a cycloalkyl group; an alkenyl group; a fluoroalkyl group; an aryl group; a hetero-cyclic group; an aralkyl group; an aralkenyl group; an alkylaryl group; an alkoxy group; an aryloxy group; a fluoroalkoxy group; a fluoroaryloxy group; an alkylamine group; a heteroarylamine group; or an arylamine group, or having no substituents. These substituents may have additional substituents.

In the present specification,

means a site linking to other substituents.

In the present specification, the halogen group includes fluorine, chlorine, bromine, iodine and the like, but is not limited thereto.

In the present specification, the alkyl group may be linear or branched, and the number of carbon atoms is not particularly limited, but is preferably 1 to 40. According to one embodiment, the alkyl group has 1 to 20 carbon atoms. According to another embodiment, the alkyl group has 1 to 10 carbon atoms. According to another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the alkenyl group may be linear or branched, and although not particularly limited, the number of carbon atoms is preferably 2 to 40. According to one embodiment, the alkenyl group has 2 to 20 carbon atoms. According to another embodiment, the alkenyl group has 2 to 10 carbon atoms. According to another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the aryl group is not particularly limited, but preferably has 6 to 60 carbon atoms, and may be a monocyclic aryl group or a multicyclic aryl group. According to one embodiment, the aryl group has 6 to 30 carbon atoms. According to one embodiment, the aryl group has 6 to 20 carbon atoms. Examples of the aryl group as a monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and two substituents may bond to each other to form a spiro structure.

When the fluorenyl group is substituted,

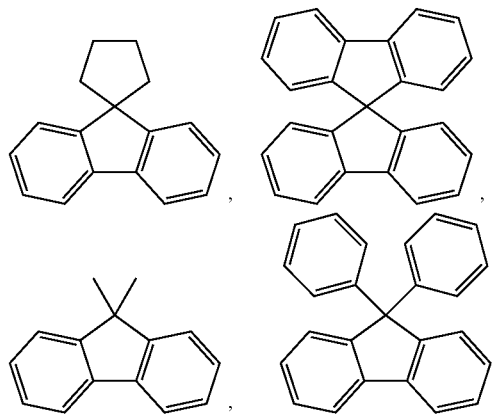

and the like may be included. However, the structure is not limited thereto.

In the present specification, the hetero-cyclic group is a hetero-cyclic group including one or more of O, N, S, Si and Se as a heteroatom, and although not particularly limited, the number of carbon atoms is preferably 2 to 60. Examples of the hetero-cyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, or a benzoimidazophenanthridine group and the like, but are not limited thereto.

In the present specification, the aryl group in the aralkyl group, the aralkenyl group, the alkylaryl group and the arylamine group is the same as the examples of the aryl group described above.

In the present specification, the alkyl group in the aralkyl group, the alkylaryl group and the alkylamine group is the same as the examples of the alkyl group described above.

In the present specification, the descriptions on the heterocyclic group made above may be used for the heteroaryl in the heteroarylamine except that the heteroaryl is aromatic.

In the present specification, the alkenyl group in the aralkenyl group is the same as the examples of the alkenyl group described above.

In the present specification, the descriptions on the aryl group made above may be used for the arylene group except that the arylene group is a divalent group.

In the present specification, the descriptions on the heterocyclic group made above may be used for the heteroarylene group except that the heteroarylene group is an aromatic divalent group.

According to one embodiment of the present specification, $B_1$ and $B_2$ are the same as or different from each other, and each independently a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, and a case in which $B_1$ and $B_2$ are all hydrogen is excluded.

The compound represented by Chemical Formula 1 according to one embodiment of the present specification has a bulkier conformation compared to a compound in which $B_1$ and $B_2$ are all hydrogen, and thereby is amorphous. Accordingly, a film formed with materials including the compound is difficult to be crystallized. In addition, the compound represented by Chemical Formula 1 has smaller molecular ionization energy compared to a case in which $B_1$ and $B_2$ are substituted with hydrogen, and thereby is capable of having high electron transfer capability, and as a result, an organic light emitting device having a little electrical short circuit is capable of being manufactured.

According to one embodiment of the present specification, $B_1$ and $B_2$ are the same as or different from each other, and each independently a substituted or unsubstituted alkyl group; or a substituted or unsubstituted aryl group.

According to one embodiment of the present specification, $B_1$ and $B_2$ are the same as or different from each other, and each independently a substituted or unsubstituted alkyl group; or a one-membered to 3-membered substituted or unsubstituted aryl group.

According to one embodiment of the present specification, $B_1$ and $B_2$ are the same as or different from each other, and each independently a substituted or unsubstituted alkyl group; or a substituted or unsubstituted phenyl group.

According to one embodiment of the present specification, $B_1$ and $B_2$ are the same as or different from each other, and each independently an alkyl group; or a phenyl group.

According to one embodiment of the present specification, $B_1$ and $B_2$ are a substituted or unsubstituted alkyl group.

According to one embodiment of the present specification, $B_1$ and $B_2$ are an alkyl group.

According to one embodiment of the present specification, $B_1$ and $B_2$ are a methyl group.

According to one embodiment of the present specification, $B_1$ and $B_2$ are a substituted or unsubstituted phenyl group.

According to one embodiment of the present specification, $B_1$ and $B_2$ are a phenyl group.

According to one embodiment of the present specification, Chemical Formula 1 may be represented by the following Chemical Formula 2.

[Chemical Formula 2]

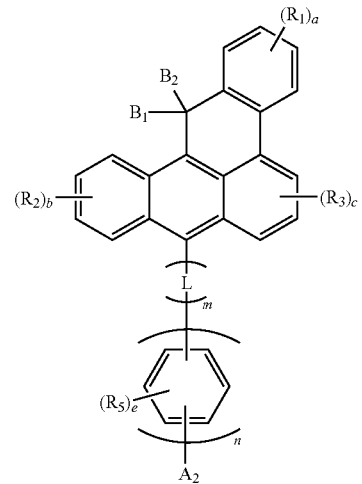

In Chemical Formula 2, definitions of $B_1$, $B_2$, L, m, $R_1$ to $R_3$, a, b and c are the same as in Chemical Formula 1, $A_2$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bonds to adjacent substituents to form a substituted or unsubstituted hydrocarbon ring or heteroring, $R_5$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, n is an integer of 0 or 1, e is an integer of 0 to 4, and when e is two or greater, $R_5$s are the same as or different from each other.

According to one embodiment of the present specification, $A_2$ in Chemical Formula 2 is hydrogen; a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ in Chemical Formula 2 is a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ in Chemical Formula 2 is a nitrile group; a pyridyl group; a benzimidazole group; or a benzoimidazophenanthridine group.

According to one embodiment of the present specification, Chemical Formula 1 may be represented by the following Chemical Formula 3.

[Chemical Formula 3]

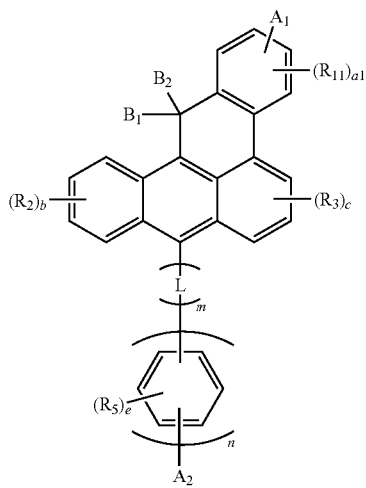

In Chemical Formula 3, definitions of $B_1$, $B_2$, L, m, $R_2$, $R_3$, b and c are the same as in Chemical Formula 1, definitions of $R_5$, $A_2$, n and e are the same as in Chemical Formula 2, $A_1$ is hydrogen; a nitrile group; a nitro group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group, or adjacent two or more substituents bond to each other to form a substituted or unsubstituted hydrocarbon ring or heteroring, $R_{11}$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, a1 is an integer of 0 to 3, and when a1 is two or greater, $R_{11}$s are the same as or different from each other.

According to one embodiment of the present specification, $A_1$ in Chemical Formula 3 is hydrogen; a nitrile group; or a substituted or unsubstituted heterocyclic group.

According to one embodiment of the present specification, $A_1$ in Chemical Formula 3 is hydrogen; a nitrile group; or a substituted or unsubstituted heteroaryl group.

According to one embodiment of the present specification, $A_1$ in Chemical Formula 3 is hydrogen; a nitrile group; a substituted or unsubstituted thiophene group; a substituted or unsubstituted furan group; a substituted or unsubstituted pyrrole group; a substituted or unsubstituted imidazole group; a substituted or unsubstituted triazole group; a substituted or unsubstituted oxazole group; a substituted or unsubstituted oxadiazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazine group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted carbazole group; a substituted or unsubstituted benzoxazole group; a substituted or unsubstituted benzimidazole group; a substituted or unsubstituted benzothiazole group; a substituted or unsubstituted benzocarbazole group; a substituted or unsubstituted benzothiophene group; a substituted or unsubstituted dibenzothiophene group; a substituted or unsubstituted benzofuranyl group; a substituted or unsubstituted phenanthroline group; a substituted or unsubstituted thiazolyl group; a substituted or unsubstituted isoxazolyl group; a substituted or unsubstituted oxadiazolyl group; a substituted or unsubstituted thiadiazolyl group; a substituted or unsubstituted benzothiazolyl group; a substituted or unsubstituted phenothiazinyl group; or a substituted or unsubstituted dibenzofuranyl group.

According to one embodiment of the present specification, $A_1$ in Chemical Formula 3 is hydrogen; a nitrile group; a thiophene group; a furan group; a pyrrole group; an imidazole group; a triazole group; an oxazole group; an oxadiazole group; a triazole group; a pyridyl group; a bipyridyl group; a pyrimidyl group; a triazine group; an acridyl group; a pyridazine group; a pyrazinyl group; a quinolinyl group; a quinazoline group; a quinoxalinyl group; a phthalazinyl group; a pyridopyrimidinyl group; a pyridopyrazinyl group; a pyrazinopyrazinyl group; an isoquinoline group; an indole group; a carbazole group; a benzoxazole group; a benzimidazole group; a benzothiazole group; a benzocarbazole group; a benzothiophene group; a dibenzothiophene group; a benzofuranyl group; a phenanthroline group; a thiazolyl group; an isoxazolyl group; an oxadiazolyl group; a thiadiazolyl group; a benzothiazolyl group; a phenothiazinyl group; or a dibenzofuranyl group.

According to one embodiment of the present specification, $A_1$ in Chemical Formula 3 is hydrogen; a nitrile group; a substituted or unsubstituted pyridyl group; or a substituted or unsubstituted benzimidazole group.

According to one embodiment of the present specification, $A_1$ in Chemical Formula 3 is hydrogen; a nitrile group; a pyridyl group; or a benzimidazole group.

According to one embodiment of the present specification, $A_2$ in Chemical Formula 3 is hydrogen; a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ in Chemical Formula 3 is a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ in Chemical Formula 3 is a nitrile group; a pyridyl group; a benzimidazole group; or a benzoimidazophenanthridine group.

According to one embodiment of the present specification, $A_1$ and $A_2$ in Chemical Formula 3 may be selected from among the following structures.

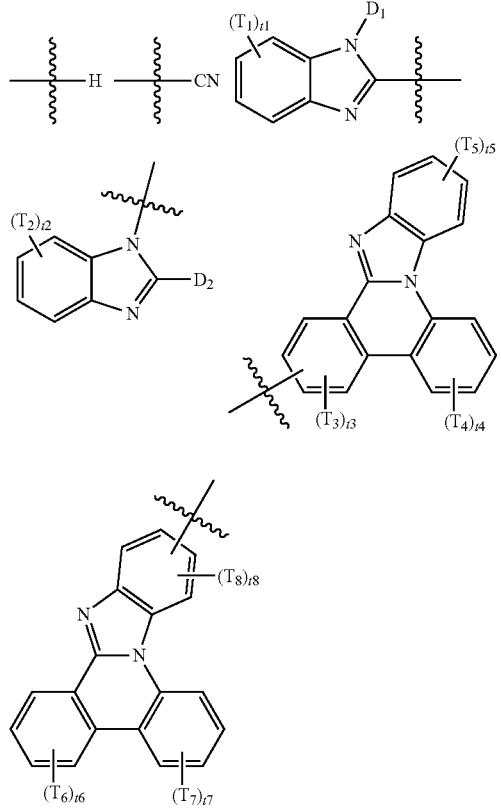

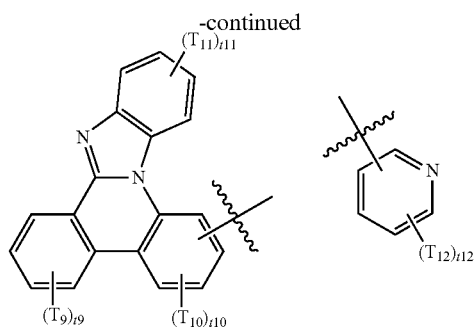

In the structures, $T_1$ to $T_{12}$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $D_1$ and $D_2$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, t1, t2, t4, t5, t6, t7, t9, t11 and t12 are the same as or different from each other, and each independently an integer of 0 to 4, t3, t8 and t10 are the same as or different from each other, and each independently an integer of 0 to 3, when t1 is two or greater, $T_1$s are the same as or different from each other, when t2 is two or greater, $T_2$s are the same as or different from each other, when t3 is two or greater, $T_3$s are the same as or different from each other, when t4 is two or greater, $T_4$s are the same as or different from each other, when t5 is two or greater, $T_5$s are the same as or different from each other, when t6 is two or greater, $T_6$s are the same as or different from each other, when t7 is two or greater, $T_7$s are the same as or different from each other, when t8 is two or greater, $T_8$s are the same as or different from each other, when t9 is two or greater, $T_9$s are the same as or different from each other, when t10 is two or greater, $T_{10}$s are the same as or different from each other, when t11 is two or greater, $T_{11}$s are the same as or different from each other, and when t12 is two or greater, $T_{12}$s are the same as or different from each other.

According to one embodiment of the present specification, $D_1$ and $D_2$ in Chemical Formula 2 are the same as or different from each other, and each independently a substituted or unsubstituted alkyl group; or a substituted or unsubstituted aryl group.

According to one embodiment of the present specification, $D_1$ and $D_2$ in Chemical Formula 2 are the same as or different from each other, and each independently a substituted or unsubstituted alkyl group having 1 to 10 carbon atoms; or a substituted or unsubstituted aryl group having 6 to 20 carbon atoms.

According to one embodiment of the present specification, $D_1$ and $D_2$ in Chemical Formula 2 are the same as or different from each other, and each independently a substituted or unsubstituted alkyl group having 1 to 6 carbon atoms; or a substituted or unsubstituted phenyl group.

According to one embodiment of the present specification, $D_1$ and $D_2$ in Chemical Formula 2 are the same as or different from each other, and each independently an alkyl group; or a phenyl group.

According to one embodiment of the present specification, $B_1$ and $B_2$ in Chemical Formula 1 are the same as or different from each other, and each independently a substituted or unsubstituted alkyl group; or a substituted or unsubstituted aryl group.

According to one embodiment of the present specification, $B_1$ and $B_2$ in Chemical Formula 1 are the same as or different from each other, and each independently an alkyl group; or an aryl group.

According to one embodiment of the present specification, $B_1$ and $B_2$ in Chemical Formula 1 are the same as or different from each other, and each independently a substituted or unsubstituted alkyl group having 1 to 10 carbon atoms; or a substituted or unsubstituted aryl group having 6 to 20 carbon atoms.

According to one embodiment of the present specification, $B_1$ and $B_2$ in Chemical Formula 1 are the same as or different from each other, and each independently a substituted or unsubstituted alkyl group having 1 to 6 carbon atoms; or a substituted or unsubstituted phenyl group.

According to one embodiment of the present specification, $B_1$ and $B_2$ in Chemical Formula 1 are the same as or different from each other, and each independently an alkyl group; or a phenyl group.

According to one embodiment of the present specification, $B_1$ and $B_2$ in Chemical Formula 1 are the same as or different from each other, and each independently a substituted or unsubstituted methyl group; or a substituted or unsubstituted phenyl group.

According to one embodiment of the present specification, $B_1$ and $B_2$ in Chemical Formula 1 are the same as or different from each other, and each independently a methyl group; or a phenyl group.

According to one embodiment of the present specification, L in Chemical Formula 1 is a substituted or unsubstituted arylene group.

According to one embodiment of the present specification, L in Chemical Formula 1 is a substituted or unsubstituted arylene group having 6 to 20 carbon atoms.

According to one embodiment of the present specification, L in Chemical Formula 1 is a substituted or unsubstituted phenyl group; a substituted or unsubstituted naphthyl group; or a substituted or unsubstituted fluorenyl group.

According to one embodiment of the present specification, L in Chemical Formula 1 is a phenyl group; a naphthyl group; or a fluorenyl group.

According to one embodiment of the present specification, L in Chemical Formula 1 may be selected from among the following structures.

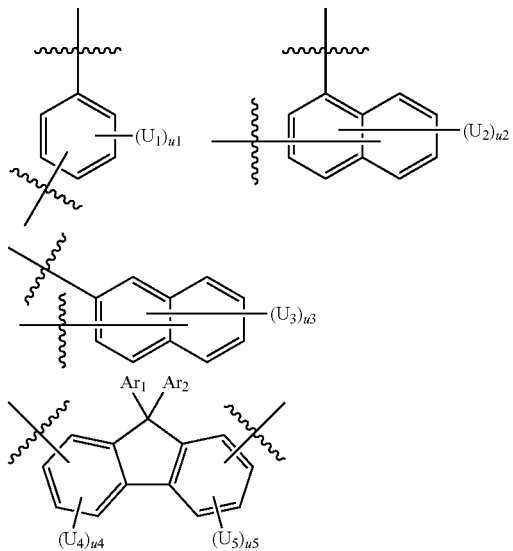

In the structures, $U_1$ to $U_5$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $Ar_1$ and $Ar_2$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, u1 is an integer of 0 to 4, u2 and u3 are the same as or different from each other, and each independently an integer of 0 to 6, u4 and u5 are the same as or different from each other, and each independently an integer of 0 to 3, when u1 is two or greater, $U_1$s are the same as or different from each other, when u2 is two or greater, $U_2$s are the same as or different from each other, when u3 is two or greater, $U_3$s are the same as or different from each other, when u4 is two or greater, $U_4$s are the same as or different from each other, and when u5 is two or greater, $U_5$s are the same as or different from each other.

According to one embodiment of the present specification, Chemical Formula 1 may be represented by the following Chemical Formula 4 or 5.

[Chemical Formula 4]

[Chemical Formula 5]

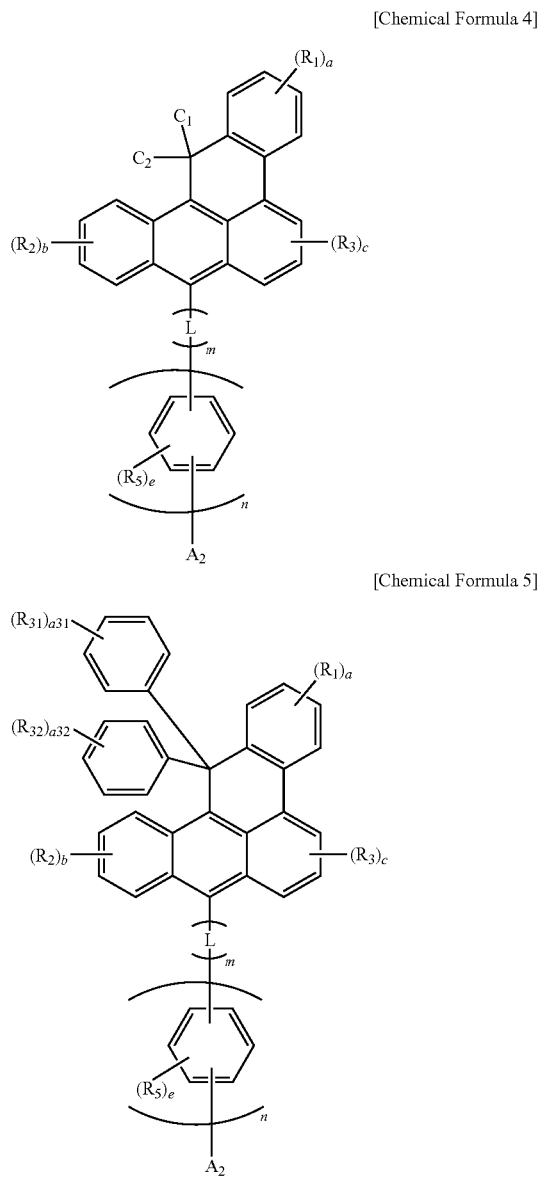

In Chemical Formulae 4 and 5, definitions of L, m, $R_1$ to $R_3$, a, b and c are the same as in Chemical Formula 1, definitions of $R_5$, $A_2$, n and e are the same as in Chemical Formula 2, $R_{31}$ and $R_{32}$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $C_1$ and $C_2$ are the same as or different from each other, and each independently a substituted or unsubstituted alkyl group, a31 and a32 are the same as or different from each other, and each independently an integer of 0 to 5, when a31 is two or greater, $R_{31}$s are the same as or different from each other, and when a32 is two or greater, $R_{32}$s are the same as or different from each other.

According to one embodiment of the present specification, Chemical Formula 1 may be represented by any one of the following Chemical Formulae 6 to 9.

[Chemical Formula 6]

[Chemical Formula 7]

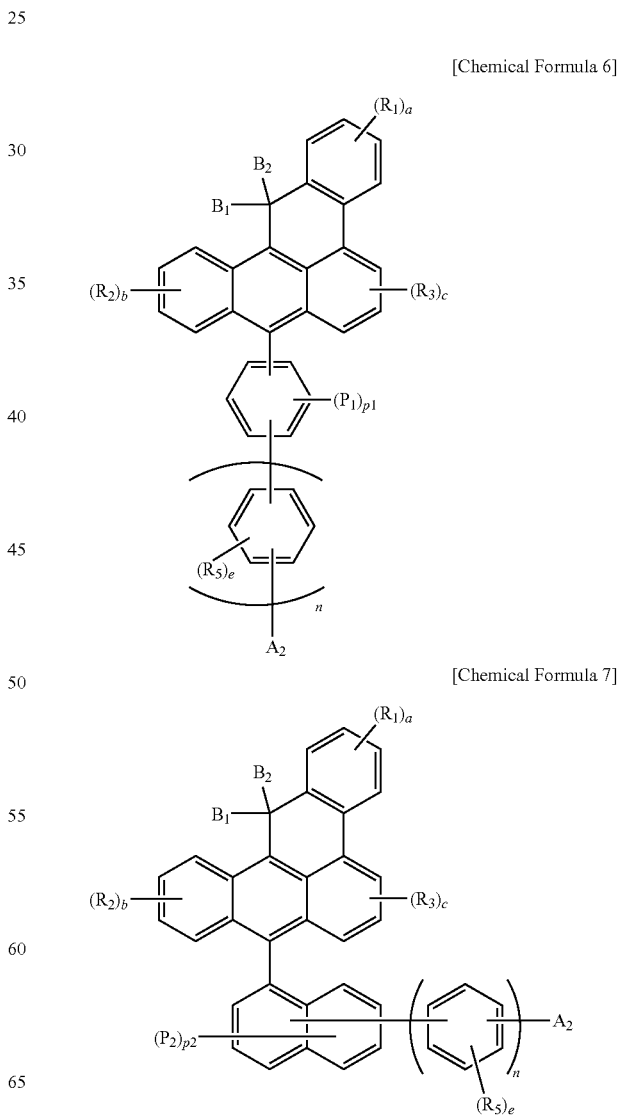

[Chemical Formula 8]

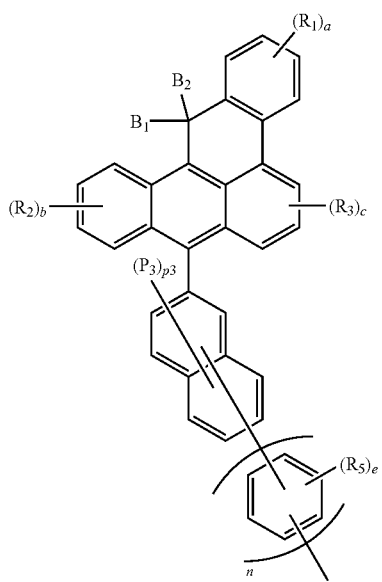

[Chemical Formula 9]

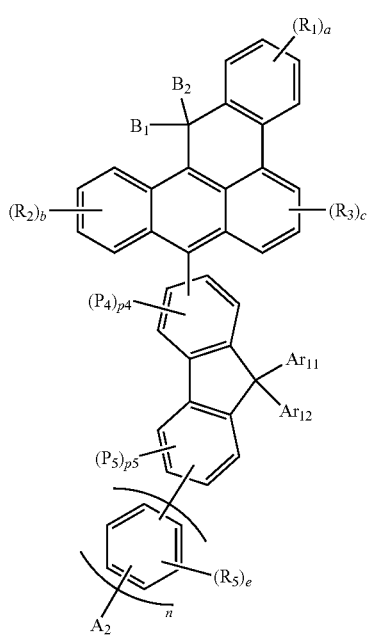

In Chemical Formulae 6 to 9, definitions of $B_1$, $B_2$, $R_1$ to $R_3$, a, b and c are the same as in Chemical Formula 1, definitions of $R_5$, $A_2$, n and e are the same as in Chemical Formula 2, $Ar_{11}$ and $Ar_{12}$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, $P_1$ to $P_5$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, p1 is an integer of 0 to 4, p2 and p3 are the same as or different from each other, and each independently an integer of 0 to 6, p4 and p5 are the same as or different from each other, and each independently an integer of 0 to 3, when p1 is two or greater, $P_1$s are the same as or different from each other, when p2 is two or greater, $P_2$s are the same as or different from each other, when p3 is two or greater, $P_3$s are the same as or different from each other, when p4 is two or greater, $P_4$s are the same as or different from each other, and when p5 is two or greater, $P_5$s are the same as or different from each other.

According to one embodiment of the present specification, $R_1$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring.

According to one embodiment of the present specification, $R_1$ is hydrogen; a nitrile group; a substituted or unsubstituted aryl group having 6 to 20 carbon atoms; or a substituted or unsubstituted heterocyclic group having 2 to 30 carbon atoms.

According to one embodiment of the present specification, $R_1$ is hydrogen; a nitrile group; or a substituted or unsubstituted heterocyclic group.

According to one embodiment of the present specification, $R_1$ is hydrogen; a nitrile group; or a substituted or unsubstituted heterocyclic group including one or more of N, O and S atoms.

According to one embodiment of the present specification, $R_1$ is hydrogen; a nitrile group; or a substituted or unsubstituted heterocyclic group including one or more N atoms.

According to one embodiment of the present specification, $R_1$ is hydrogen; a nitrile group; or a substituted or unsubstituted heteroaryl group.

According to one embodiment of the present specification, $R_1$ is hydrogen; a nitrile group; a substituted or unsubstituted thiophene group; a substituted or unsubstituted furan group; a substituted or unsubstituted pyrrole group; a substituted or unsubstituted imidazole group; a substituted or unsubstituted triazole group; a substituted or unsubstituted oxazole group; a substituted or unsubstituted oxadiazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazine group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted carbazole group; a substituted or unsubstituted benzoxazole group; a substituted or unsubstituted benzimidazole group; a substituted or unsubstituted benzothiazole group; a substituted or unsubstituted benzocarbazole group; a substituted or unsubstituted benzothiophene group; a substituted or unsubstituted dibenzothiophene group; a substituted or unsubstituted benzofuranyl group; a substituted or unsubstituted phenanthroline group; a substituted or unsubstituted thiazolyl group; a substituted or unsubstituted isoxazolyl group; a substituted or unsubstituted oxadiazolyl group; a substituted or unsubstituted thiadiazolyl group; a substituted or unsubstituted benzothiazolyl group; a substituted or unsubstituted phenothiazinyl group; or a substituted or unsubstituted dibenzofuranyl group.

According to one embodiment of the present specification, $R_1$ is hydrogen; a nitrile group; a thiophene group; a furan group; a pyrrole group; an imidazole group; a triazole group; an oxazole group; an oxadiazole group; a triazole group; a pyridyl group; a bipyridyl group; a pyrimidyl group; a triazine group; an acridyl group; a pyridazine group; a pyrazinyl group; a quinolinyl group; a quinazoline group; a quinoxalinyl group; a phthalazinyl group; a pyridopyrimidinyl group; a pyridopyrazinyl group; a pyrazinopyrazinyl group; an isoquinoline group; an indole group; a carbazole group; a benzoxazole group; a benzimidazole group; a benzothiazole group; a benzocarbazole group; a benzothiophene group; a dibenzothiophene group; a benzofuranyl group; a phenanthroline group; a thiazolyl group; an isoxazolyl group; an oxadiazolyl group; a thiadiazolyl group; a benzothiazolyl group; a phenothiazinyl group; or a dibenzofuranyl group.

According to one embodiment of the present specification, $R_1$ is hydrogen; a nitrile group; a substituted or unsubstituted pyridyl group; or a substituted or unsubstituted benzimidazole group.

According to one embodiment of the present specification, $R_1$ is hydrogen; a nitrile group; a pyridyl group; or a benzimidazole group.

According to one embodiment of the present specification, $A_2$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group.

According to one embodiment of the present specification, $A_2$ is hydrogen; a nitrile group; or a substituted or unsubstituted heterocyclic group.

According to one embodiment of the present specification, $A_2$ is hydrogen; a nitrile group; or a substituted or unsubstituted heterocyclic group including one or more of N, O and S atoms.

According to one embodiment of the present specification, $A_2$ is hydrogen; a nitrile group; or a substituted or unsubstituted heterocyclic group including one or more N atoms.

According to one embodiment of the present specification, $A_2$ is hydrogen; a nitrile group; or a substituted or unsubstituted heteroaryl group.

According to one embodiment of the present specification, $A_2$ is hydrogen; a nitrile group; a substituted or unsubstituted thiophene group; a substituted or unsubstituted furan group; a substituted or unsubstituted pyrrole group; a substituted or unsubstituted imidazole group; a substituted or unsubstituted triazole group; a substituted or unsubstituted oxazole group; a substituted or unsubstituted oxadiazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazine group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted carbazole group; a substituted or unsubstituted benzoxazole group; a substituted or unsubstituted benzimidazole group; a substituted or unsubstituted benzothiazole group; a substituted or unsubstituted benzocarbazole group; a substituted or unsubstituted benzothiophene group; a substituted or unsubstituted dibenzothiophene group; a substituted or unsubstituted benzofuranyl group; a substituted or unsubstituted phenanthroline group; a substituted or unsubstituted thiazolyl group; a substituted or unsubstituted isoxazolyl group; a substituted or unsubstituted oxadiazolyl group; a substituted or unsubstituted thiadiazolyl group; a substituted or unsubstituted benzothiazolyl group; a substituted or unsubstituted phenothiazinyl group; a substituted or unsubstituted dibenzofuranyl group; or a substituted or unsubstituted benzoimidazophenanthridine group.

According to one embodiment of the present specification, $A_2$ is hydrogen; a nitrile group; a thiophene group; a furan group; a pyrrole group; an imidazole group; a triazole group; an oxazole group; an oxadiazole group; a triazole group; a pyridyl group; a bipyridyl group; a pyrimidyl group; a triazine group; an acridyl group; a pyridazine group; a pyrazinyl group; a quinolinyl group; a quinazoline group; a quinoxalinyl group; a phthalazinyl group; a pyridopyrimidinyl group; a pyridopyrazinyl group; a pyrazinopyrazinyl group; an isoquinoline group; an indole group; a carbazole group; a benzoxazole group; a benzimidazole group; a benzothiazole group; a benzocarbazole group; a benzothiophene group; a dibenzothiophene group; a benzofuranyl group; a phenanthroline group; a thiazolyl group; an isoxazolyl group; an oxadiazolyl group; a thiadiazolyl group; a benzothiazolyl group; a phenothiazinyl group; a dibenzofuranyl group; or a benzoimidazophenanthridine group.

According to one embodiment of the present specification, $A_2$ is hydrogen; a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ is a nitrile group; a substituted or unsubstituted pyridyl group; a substituted or unsubstituted benzimidazole group; or a substituted or unsubstituted benzoimidazophenanthridine group.

According to one embodiment of the present specification, $A_2$ is a nitrile group; a pyridyl group; or a benzimidazole group; or a benzoimidazophenanthridine group.

According to one embodiment of the present specification, m is an integer of 0 to 5.

According to one embodiment of the present specification, m is an integer of 0 or 1.

According to one embodiment of the present specification, $R_2$ and $R_3$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring.

According to one embodiment of the present specification, $R_2$ and $R_3$ are the same as or different from each other, and each independently hydrogen; deuterium; a substituted or unsubstituted alkyl group; a substituted or unsubstituted aryl group; or a substituted or unsubstituted heterocyclic group.

According to one embodiment of the present specification, $R_2$ and $R_3$ are the same as or different from each other, and each independently hydrogen; deuterium; a substituted or unsubstituted alkyl group having 1 to 6 carbon atoms; a substituted or unsubstituted aryl group having 6 to 20 carbon atoms; or a substituted or unsubstituted heterocyclic group having 2 to 30 atoms.

According to one embodiment of the present specification, $R_2$ and $R_3$ are hydrogen.

According to one embodiment of the present specification, $R_4$s are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring.

According to one embodiment of the present specification, $R_4$ is hydrogen; a nitrile group; or a substituted or unsubstituted heterocyclic group.

According to one embodiment of the present specification, $R_4$ is hydrogen; a nitrile group; or a substituted or unsubstituted heterocyclic group including one or more of N, O and S atoms.

According to one embodiment of the present specification, $R_4$ is hydrogen; a nitrile group; or a substituted or unsubstituted heterocyclic group including one or more N atoms.

According to one embodiment of the present specification, $R_4$ is hydrogen; a nitrile group; or a substituted or unsubstituted heteroaryl group.

According to one embodiment of the present specification, $R_4$ is hydrogen; a nitrile group; a substituted or unsubstituted thiophene group; a substituted or unsubstituted furan group; a substituted or unsubstituted pyrrole group; a substituted or unsubstituted imidazole group; a substituted or unsubstituted triazole group; a substituted or unsubstituted oxazole group; a substituted or unsubstituted oxadiazole group; a substituted or unsubstituted triazole group; a substituted or unsubstituted pyridyl group; a substituted or unsubstituted bipyridyl group; a substituted or unsubstituted pyrimidyl group; a substituted or unsubstituted triazine group; a substituted or unsubstituted acridyl group; a substituted or unsubstituted pyridazine group; a substituted or unsubstituted pyrazinyl group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted carbazole group; a substituted or unsubstituted benzoxazole group; a substituted or unsubstituted benzimidazole group; a substituted or unsubstituted benzothiazole group; a substituted or unsubstituted benzocarbazole group; a substituted or unsubstituted benzothiophene group; a substituted or unsubstituted dibenzothiophene group; a substituted or unsubstituted benzofuranyl group; a substituted or unsubstituted phenanthroline group; a substituted or unsubstituted thiazolyl group; a substituted or unsubstituted isoxazolyl group; a substituted or unsubstituted oxadiazolyl group; a substituted or unsubstituted thiadiazolyl group; a substituted or unsubstituted benzothiazolyl group; a substituted or unsubstituted phenothiazinyl group; a substituted or unsubstituted dibenzofuranyl group; or a substituted or unsubstituted benzoimidazophenanthridine group.

According to one embodiment of the present specification, $R_4$ is hydrogen; a nitrile group; a thiophene group; a furan group; a pyrrole group; an imidazole group; a triazole group; an oxazole group; an oxadiazole group; a triazole group; a pyridyl group; a bipyridyl group; a pyrimidyl group; a triazine group; an acridyl group; a pyridazine group; a pyrazinyl group; a quinolinyl group; a quinazoline group; a quinoxalinyl group; a phthalazinyl group; a pyridopyrimidinyl group; a pyridopyrazinyl group; a pyrazinopyrazinyl group; an isoquinoline group; an indole group; a carbazole group; a benzoxazole group; a benzimidazole group; a benzothiazole group; a benzocarbazole group; a benzothiophene group; a dibenzothiophene group; a benzofuranyl group; a phenanthroline group; a thiazolyl group; an isoxazolyl group; an oxadiazolyl group; a thiadiazolyl group; a benzothiazolyl group; a phenothiazinyl group; a dibenzofuranyl group; or a benzoimidazophenanthridine group.

According to one embodiment of the present specification, $R_4$ is hydrogen; a nitrile group; a substituted or unsubstituted pyridyl group; a substituted or unsubstituted benzimidazole group; or a substituted or unsubstituted benzoimidazophenanthridine group.

According to one embodiment of the present specification, $R_4$ is a nitrile group; a substituted or unsubstituted pyridyl group; a substituted or unsubstituted benzimidazole group; or a substituted or unsubstituted benzoimidazophenanthridine group.

According to one embodiment of the present specification, $R_4$ is a nitrile group; a pyridyl group; or a benzimidazole group; or a benzoimidazophenanthridine group.

1

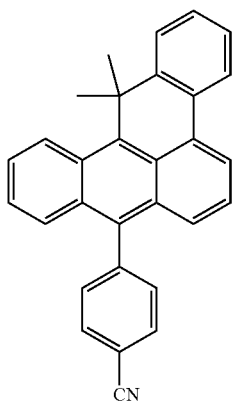

2

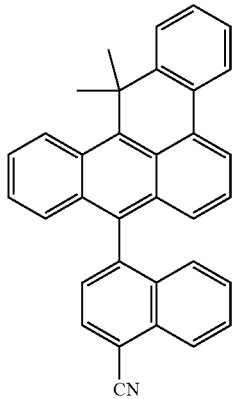

3

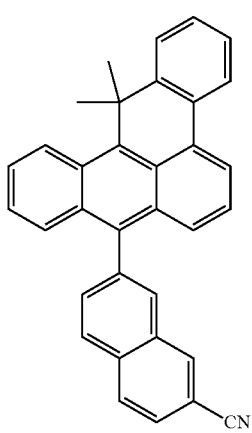

-continued

4

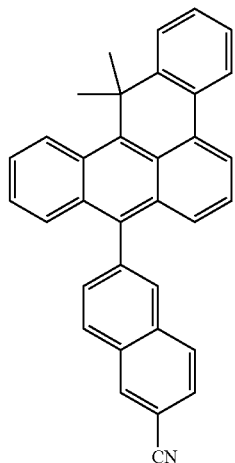

5

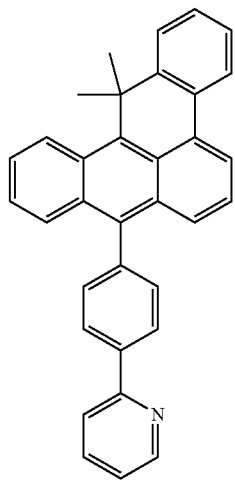

6

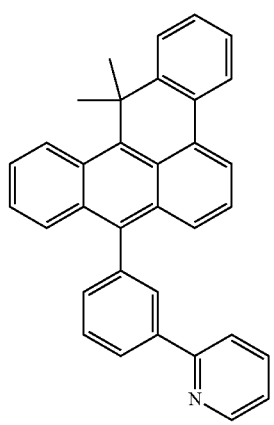

7
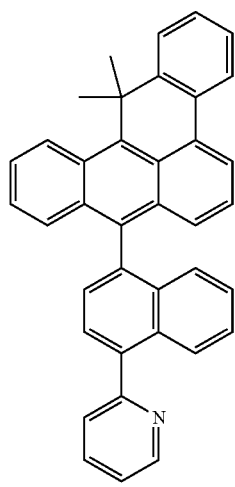
8
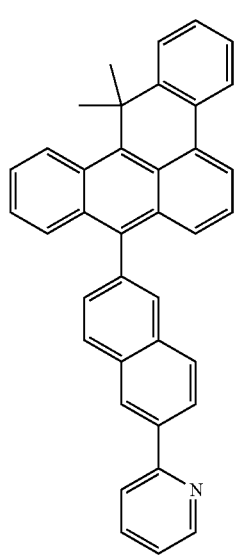
9
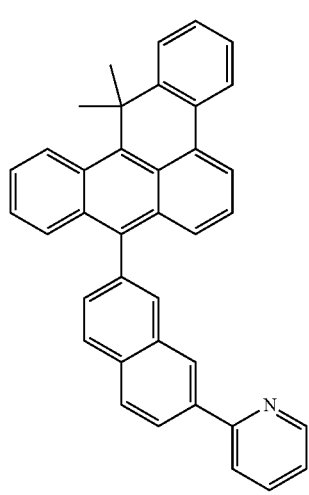
10
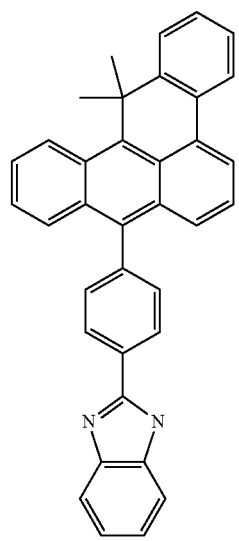
11
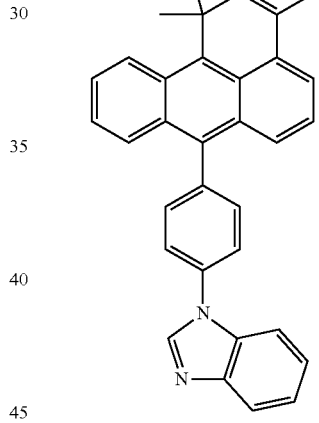
12
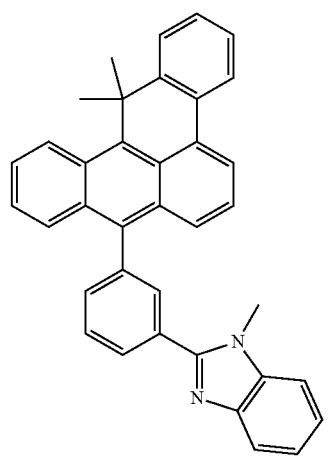

13
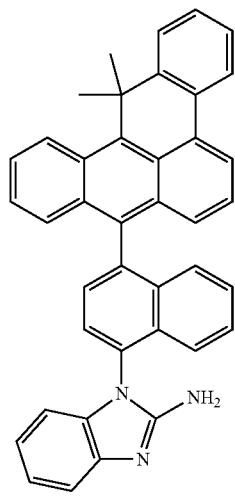
14
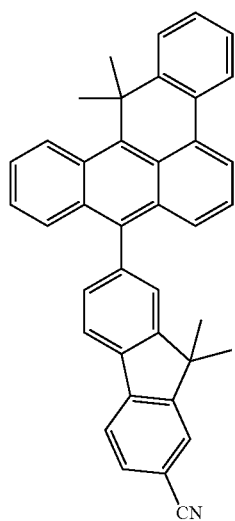
15
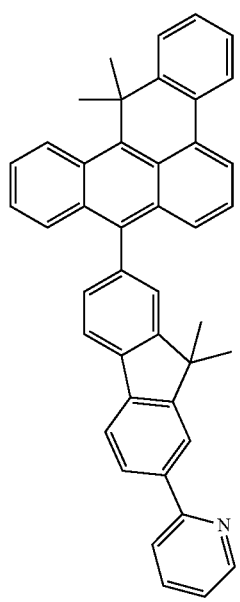
16
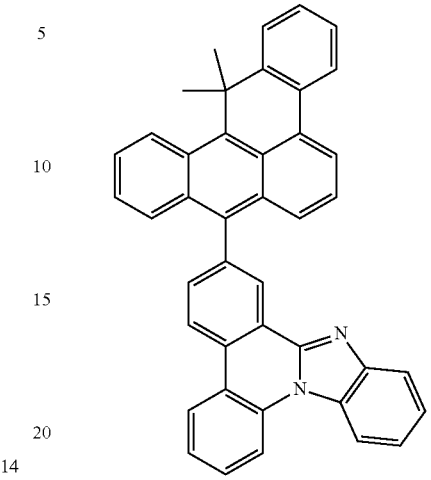
17
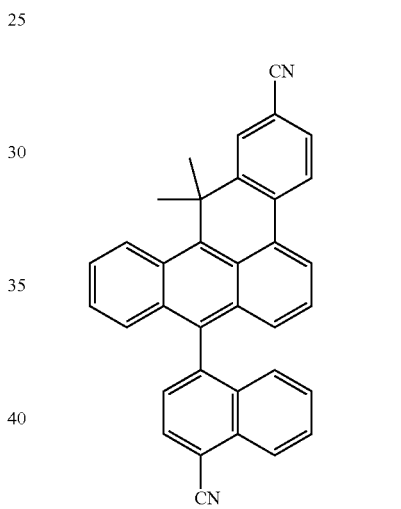
18
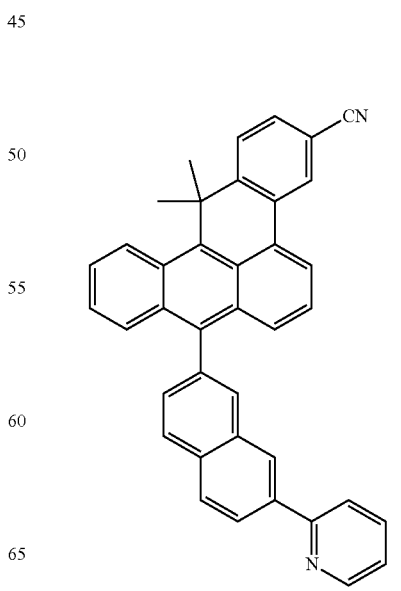

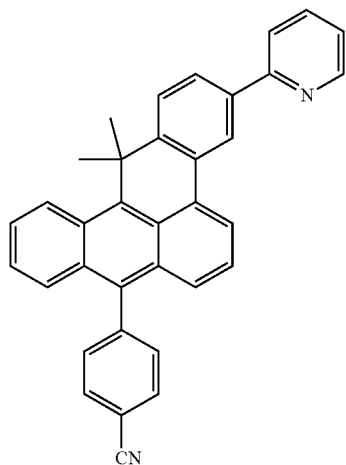
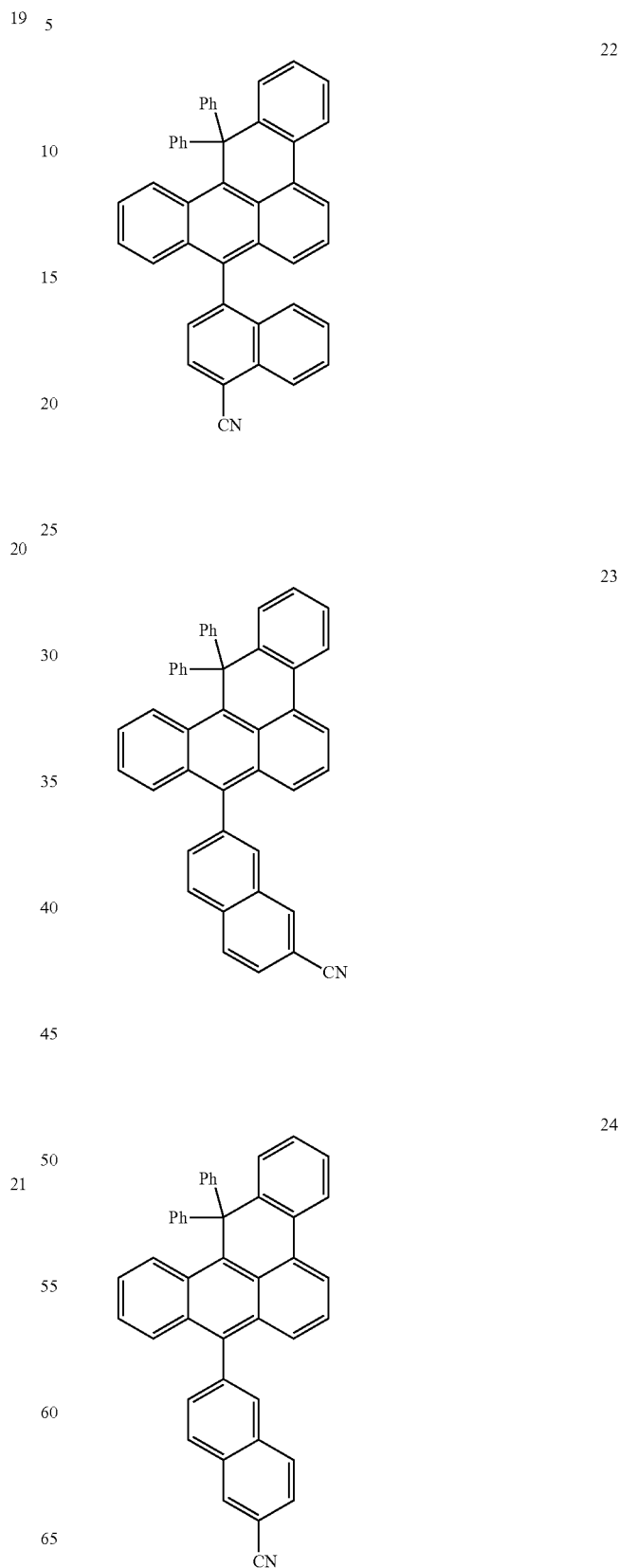

25
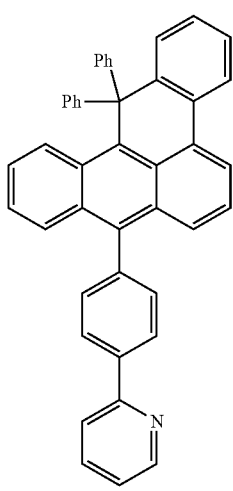
26
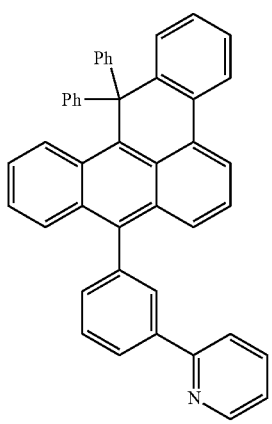
27
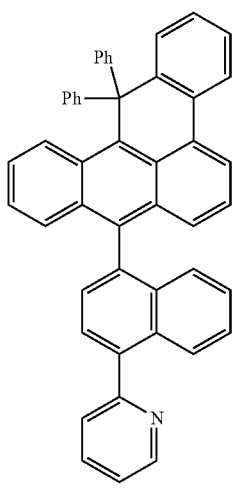
28
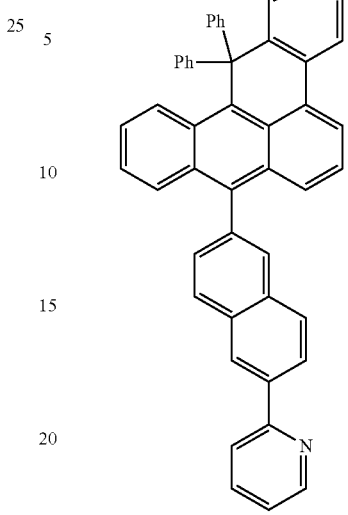
29
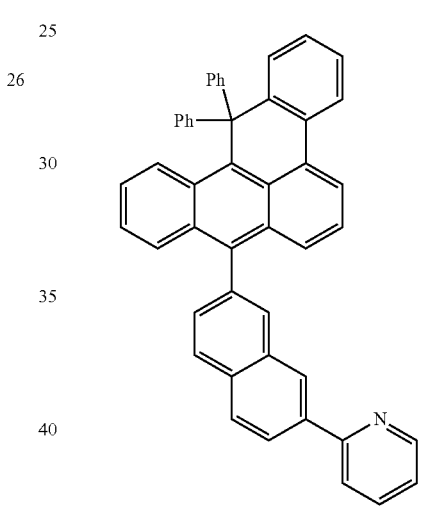
30
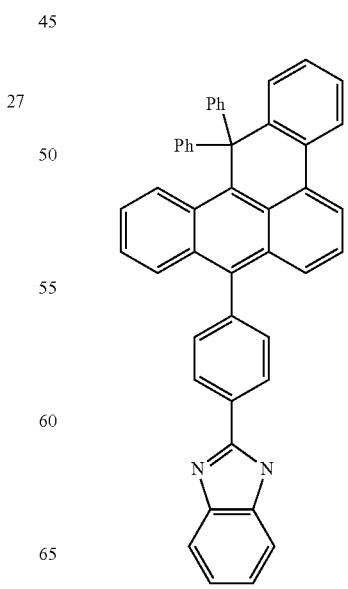

31
-continued
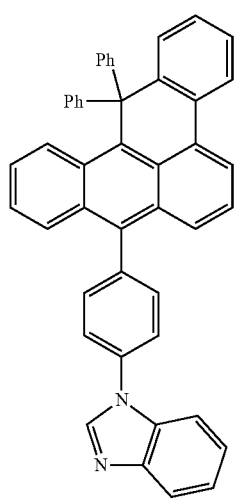
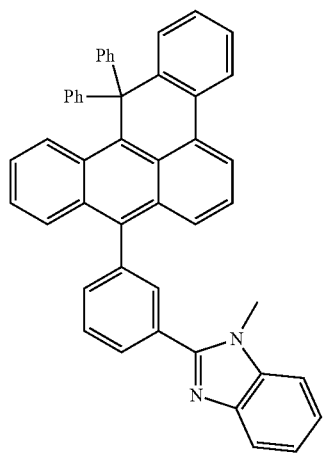
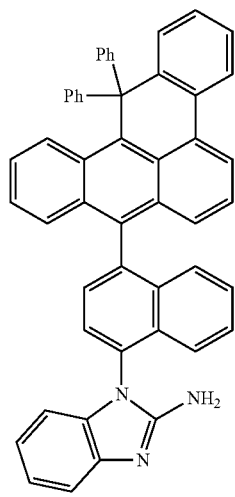
32
-continued
31
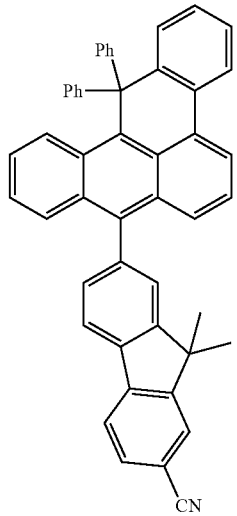
32
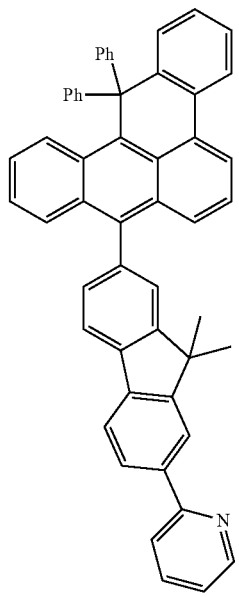
33
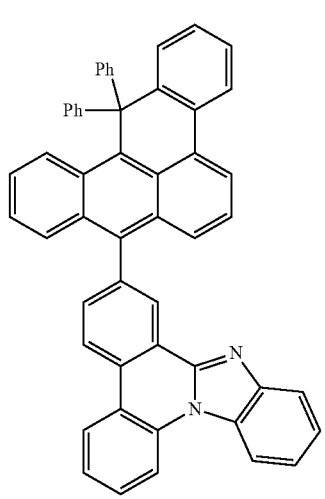
34
35
36

37

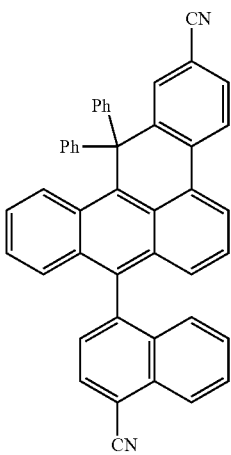

38

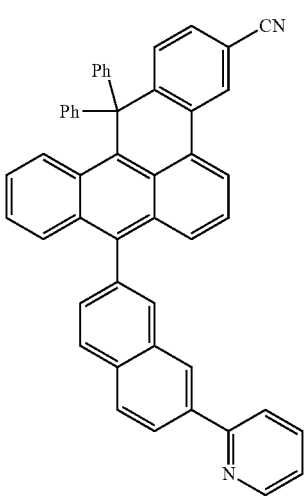

39

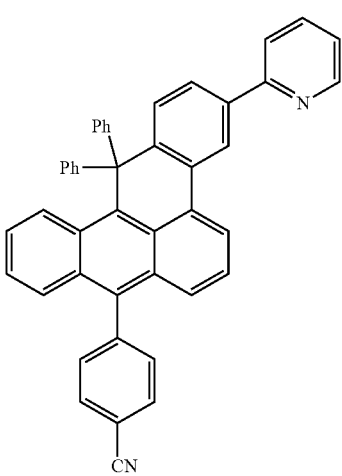

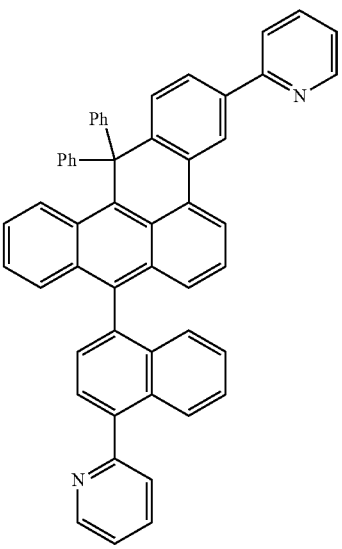

40

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a monolayer structure, but may also be formed in a multilayer structure in which two or more organic material layers are laminated. For example, the organic light emitting device of the present invention may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer, a hole transfer layer or a layer carrying out hole injection and transfer at the same time.

In another embodiment, the organic material layer includes a light emitting layer.

In one embodiment of the present specification, the organic material layer includes an electron transfer layer or an electron injection layer, and the electron transfer layer includes the compound of Chemical Formula 1.

In one embodiment of the present specification, the electron transfer layer, the electron injection layer or the layer carrying out electron transfer and electron injection at the same time includes the compound of Chemical Formula 1.

In another embodiment, the organic material layer includes a light emitting layer and an electron transfer layer, and the electron transfer layer includes the compound of Chemical Formula 1.

In another embodiment, the organic light emitting device may be an organic light emitting device having a normal-type structure in which an anode, one or more organic material layers and a cathode are laminated in consecutive order on a substrate.

In another embodiment, the organic light emitting device may be an organic light emitting device having an inverted-type structure in which a cathode, one or more organic material layers and an anode are laminated in consecutive order on a substrate.

For example, the structures of an organic light emitting device according to one embodiment of the present specification are illustrated in FIGS. 1 and 2.

FIG. 1 is a diagram showing an example of an organic light emitting device formed with a substrate (1), an anode (2), a light emitting layer (3) and a cathode (4). In such a structure, the compound may be included in the light emitting layer.

FIG. 2 is a diagram showing an example of an organic light emitting device formed with a substrate (1), an anode (2), a hole injection layer (5), a hole transfer layer (6), a light emitting layer (7), an electron transfer layer (8) and a cathode (4). In such a structure, the compound may be included in the electron transfer layer.

When the organic light emitting device includes a plurality of organic material layers, the organic material layers may be formed with the same material or with different materials.

The organic light emitting device of the present specification may be manufactured using materials and methods known in the art, except that one or more layers of the organic material layers include the compound of Chemical Formula 1, that is, the compound represented by Chemical Formula 1.

For example, the organic light emitting device of the present specification may be manufactured by consecutively laminating a first electrode, an organic material layer and a second electrode on a substrate. Herein, the organic light emitting device may be manufactured by forming an anode on the substrate by depositing a metal, a metal oxide having conductivity, or alloys thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material capable of being used as a cathode thereon.

In addition, the compound of Chemical Formula 1 may be formed as the organic material layer using a solution coating method as well as a vacuum deposition method when manufacturing the organic light emitting device. Herein, the solution coating method means spin coating, dip coating, doctor blading, ink jet printing, screen printing, a spray method, roll coating and the like, but is not limited thereto.

In addition to this method, the organic light emitting device may also be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, a material having large work function is normally preferable so that hole injection to the organic material layer is smooth. Specific examples of the anode material capable of being used in the present invention include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex (Alq$_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene, and the like, but are not limited thereto.

The light emitting layer may include a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-including pyrene, anthracene, crycene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

The preparation of the compound represented by Chemical Formula 1 and the organic light emitting device including the compound will be described in detail in the following examples. However, the following examples are for illustrative purposes only, and the scope of the present specification is not limited thereto.

PREPARATION EXAMPLE 1

General Preparation Example of Compound of Chemical Formula 1

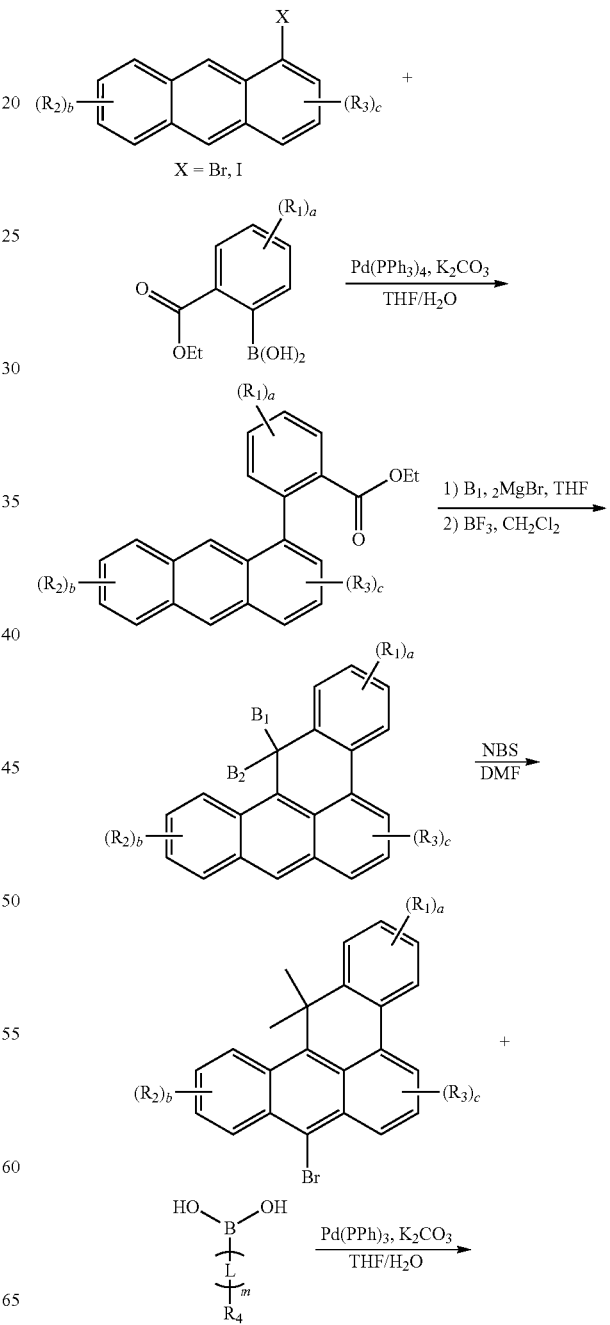

-continued

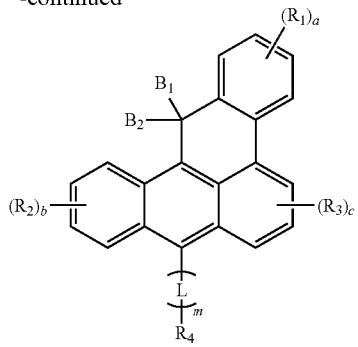

A general preparation example of the compound of Chemical Formula 1 is schematized as above. Definitions of $R_1$ to $R_4$, $B_1$, $B_2$, L, a to c, and m are the same as the definitions of the substituents of Chemical Formula 1. Specific examples of the compound are described below.

PREPARATION EXAMPLE 2

Synthesis of Compound 1

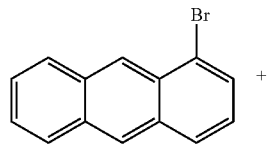

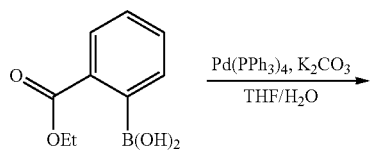

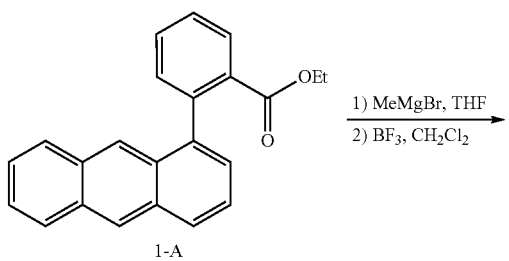

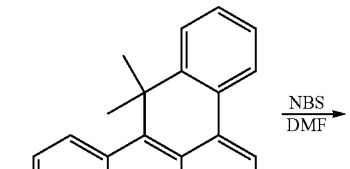

-continued

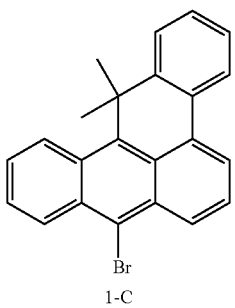

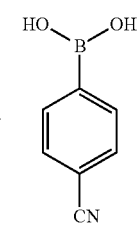

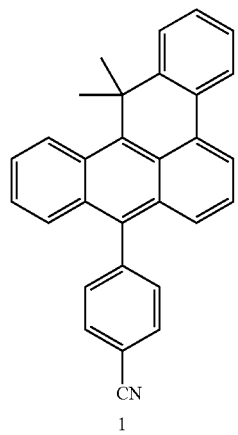

After 1-bromoanthracene (2.56 g, 10 mmol) and (2-ethoxycarbonyl)phenyl boronic acid (1.94 g, 10 mmol) were dissolved in 30 ml of THF, a solution dissolving $K_2CO_3$ (4.15 g, 30 mmol) in 10 ml of water was mixed thereto, and the result was stirred while raising a temperature. When the result started to reflux, tetrakis(triphenylphosphine)palladium (0.35 g, 0.3 mmol) was introduced thereto all at once, and the result was reacted for 24 hours. After the reaction was complete, the result was cooled, the water and the organic layer were separated, and only the organic layer was collected, dried with anhydrous magnesium sulfate, and celite filtered. The result was concentrated under vacuum, column purified and dried, and as a result, 2.90 g of 1-A was prepared.

After 1-A (2.90 g, 8.89 mmol) was dissolved in 20 ml of THF, 1.4 M methyl magnesium bromide (19.04 ml, 26.67 mmol) was slowly added dropwise thereto at room temperature. After the reaction was complete, 100 ml of water and 100 ml of ethyl acetate were each added to the result for washing, and the organic layer was collected and dried with anhydrous magnesium sulfate. Solids obtained by concentrating the organic layer under vacuum were dissolved in 25 ml of $CH_2Cl_2$, and then 0.3 ml of $BF_3$ was added thereto and the result was stirred for 30 minutes. After 2 ml of methanol was added thereto to complete the reaction, 200 ml of $CH_2Cl_2$ and 200 ml of water were each added to the result for washing, and only the organic layer was collected and dried with anhydrous magnesium sulfate. The result was concentrated under vacuum, column purified and dried, and as a result, 1.46 g of 1-B was prepared.

1-B (1.46 g, 4.96 mmol), NBS (0.97 g, 5.46 mmol) and 30 ml of DMF were stirred for 1 hour at 0° C. After the reaction was complete, the solution was concentrated under vacuum, the result was washed with 50 ml of an aqueous $Na_2S_2O_3$ solution and 100 ml of $CHCl_3$, and only the organic layer was collected and dried with anhydrous magnesium sulfate.

The result was concentrated under vacuum, column purified and dried, and as a result, 1.57 g of 1-C was prepared.

1-C (1.57 g, 4.22 mmol) and (4-cyanophenyl)boronic acid (0.62 g, 4.22 mmol) were dissolved in 20 ml of THF. A solution dissolving $K_2CO_3$ (1.75 g, 12.66 mmol) in 10 ml of water was mixed thereto, and the result was stirred while raising a temperature. When the result started to reflux, tetrakis(triphenylphosphine)palladium (0.15 g, 0.13 mmol) was introduced thereto, and the result was reacted for 24 hours. After cooling the result, the water and the organic layer were separated, and only the organic layer was collected, dried with anhydrous magnesium sulfate, and celite filtered. The result was concentrated under vacuum, column purified and dried, and as a result, 1.49 g of Compound 1 was prepared.

MS[M+H]$^+$=396

PREPARATION EXAMPLE 3

Synthesis of Compound 7

1-C (3.72 g, 10 mmol) obtained in the synthesis process of Compound 1 and (4-(pyridin-2-yl)naphthalen-1-yl)boronic acid (2.49 g, 10 mmol) were dissolved in 25 ml of THF. A solution dissolving $K_2CO_3$ (4.15 g, 30 mmol) in 10 ml of water was mixed thereto, and the result was stirred while raising a temperature. When the result started to reflux, tetrakis(triphenylphosphine)palladium (0.35 g, 0.3 mmol) was introduced thereto, and the result was reacted for 16 hours. After the reaction was complete, the result was cooled, the water and the organic layer were separated, and only the organic layer was collected, dried with anhydrous magnesium sulfate, and celite filtered. The result was concentrated under vacuum, column purified and dried, and as a result, 3.78 g of Compound 7 was prepared.

MS[M+H]$^+$=498

PREPARATION EXAMPLE 4

Synthesis of Compound 11

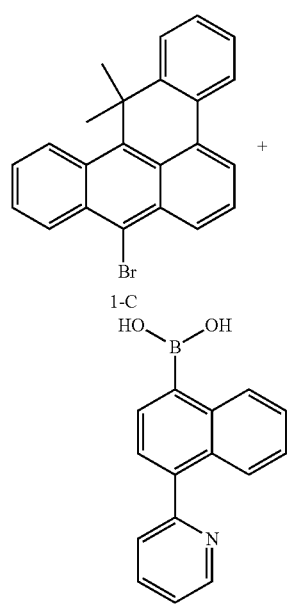
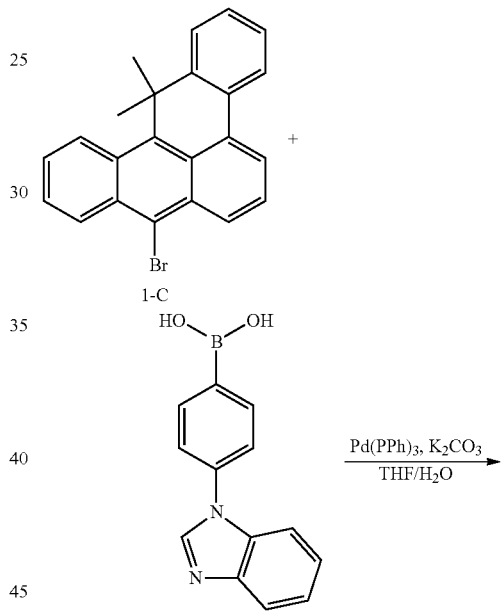
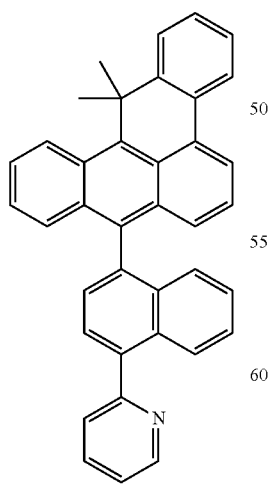
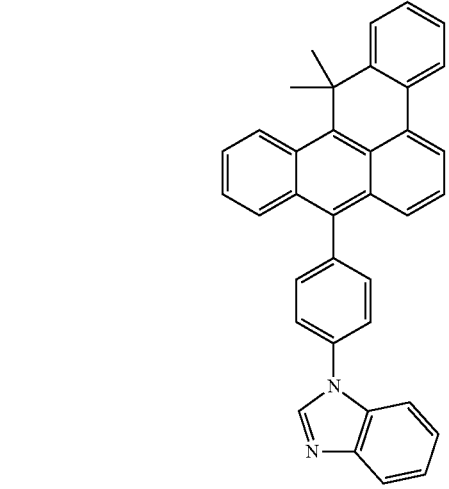

3.60 g of Compound 11 was prepared by being reacted and purified in the same manner as in the synthesis of Compound 1, except that 1-C (3.72 g, 10 mmol) obtained in the synthesis process of Compound 1 and (4-(1H-benzo[d]imidazol-1-yl)phenyl)boronic acid (2.38 g, 10 mmol) were used.

MS[M+H]$^+$=487

PREPARATION EXAMPLE 5

Synthesis of Compound 13

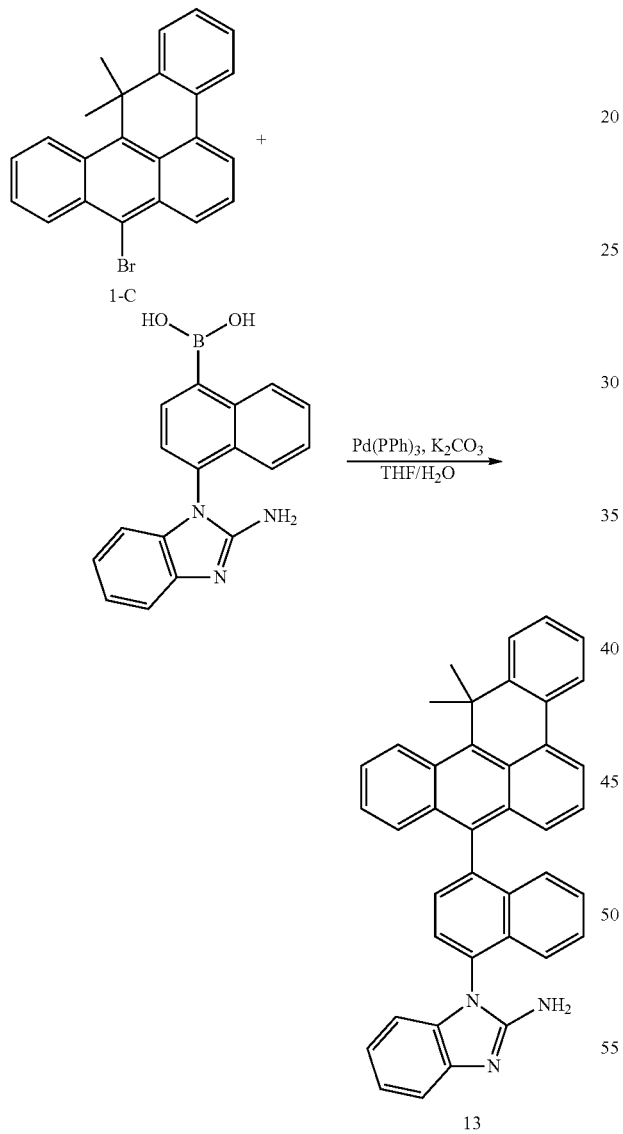

PREPARATION EXAMPLE 6

Synthesis of Compound 14

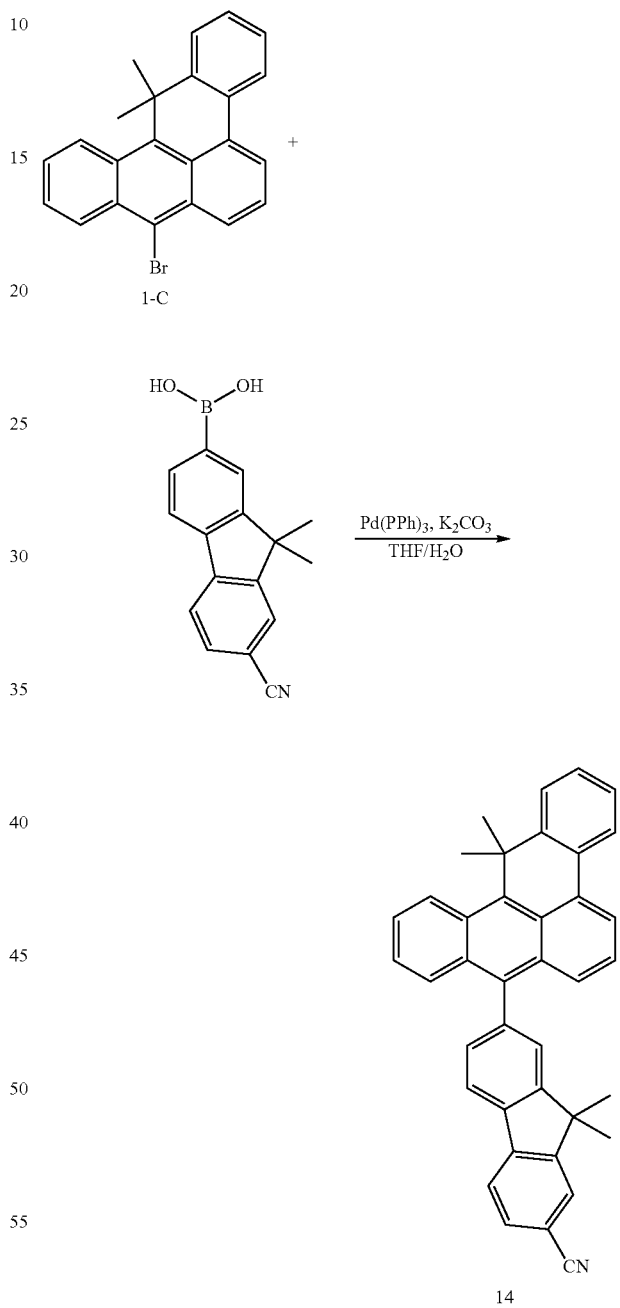

3.75 g of Compound 13 was prepared by being reacted and purified in the same manner as in the synthesis of Compound 1, except that 1-C (3.72 g, 10 mmol) obtained in the synthesis process of Compound 1 and (4-(2-amino-1H-benzo[d]imidazol-1-yl)naphthalen-1-yl)boronic acid (3.03 g, 10 mmol) were used.

MS[M+H]$^+$=552

4.04 g of Compound 14 was prepared by being reacted and purified in the same manner as in the synthesis of Compound 1, except that 1-C (3.72 g, 10 mmol) obtained in the synthesis process of Compound 1 and (7-cyano-9,9-dimethyl-9H-fluoren-2-yl)boronic acid (2.63 g, 10 mmol) were used.

MS[M+H]$^+$=512

PREPARATION EXAMPLE 7

Synthesis of Compound 17

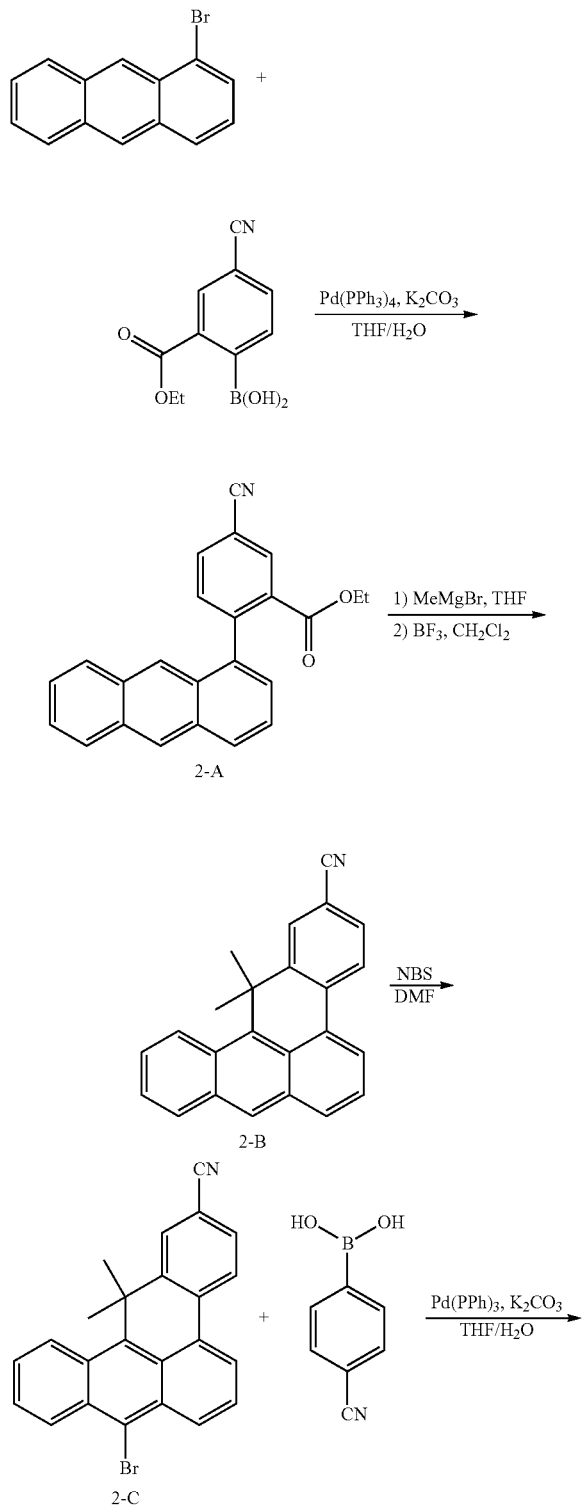

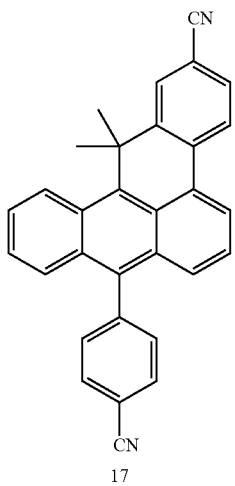

After 1-bromoanthracene (2.56 g, 10 mmol) and (4-cyano-2-(ethoxycarbonyl) phenyl)boronic acid (2.19 g, 10 mmol) were dissolved in 30 ml of THF, a solution dissolving $K_2CO_3$ (4.15 g, 30 mmol) in 10 ml of water was mixed thereto, and the result was stirred while raising a temperature. When the result started to reflux, tetrakis(triphenylphosphine)palladium (0.35 g, 0.3 mmol) was introduced thereto all at once, and the result was reacted for 18 hours. After the reaction was complete, the result was cooled, the water and the organic layer were separated, and only the organic layer was collected, dried with anhydrous magnesium sulfate, and celite filtered. The result was concentrated under vacuum, column purified and dried, and as a result, 2.77 g of 2-A was prepared.

After 2-A (2.77 g, 7.89 mmol) was dissolved in 20 ml of THF, 1.4 M methyl magnesium bromide (16.90 ml, 23.67 mmol) was slowly added dropwise thereto at room temperature. After the reaction was complete, 100 ml of water and 100 ml of ethyl acetate were each added to the result for washing, and the organic layer was collected and dried with anhydrous magnesium sulfate. Solids obtained by concentrating the organic layer under vacuum were dissolved in 25 ml of $CH_2Cl_2$, and then 0.3 ml of $BF_3$ was added thereto and the result was stirred for 30 minutes. After 2 ml of methanol was added thereto to complete the reaction, 200 ml of $CH_2Cl_2$ and 200 ml of water were each added to the result for washing, and only the organic layer was collected and dried with anhydrous magnesium sulfate. The result was concentrated under vacuum, column purified and dried, and as a result, 1.59 g of 2-B was prepared.

2-B (1.59 g, 4.98 mmol), NBS (0.97 g, 5.48 mmol) and 30 ml of DMF were stirred for 1 hour at 0° C. After the reaction was complete, the solution was concentrated under vacuum, the result was washed with 50 ml of an aqueous $Na_2S_2O_3$ solution and 100 ml of $CHCl_3$, and only the organic layer was collected and dried with anhydrous magnesium sulfate. The result was concentrated under vacuum, column purified and dried, and as a result, 1.58 g of 2-C was prepared.

2-C (1.58 g, 3.98 mmol) and (4-cyanophenyl)boronic acid (0.59 g, 3.98 mmol) were dissolved in 20 ml of THF. A solution dissolving $K_2CO_3$ (1.65 g, 11.94 mmol) in 10 ml of water was mixed thereto, and the result was stirred while raising a temperature. When the result started to reflux, tetrakis(triphenylphosphine)palladium (0.14 g, 0.12 mmol) was introduced thereto, and the result was reacted for 19 hours. After cooling the result, the water and the organic layer were separated, and only the organic layer was collected, dried with anhydrous magnesium sulfate, and celite filtered. The result was concentrated under vacuum, column purified and dried, and as a result, 1.34 g of Compound 17 was prepared.

MS[M+H]$^+$=421

PREPARATION EXAMPLE 8

Synthesis of Compound 21

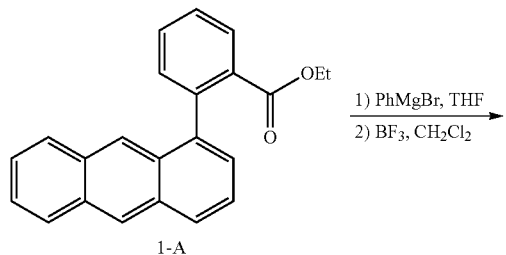

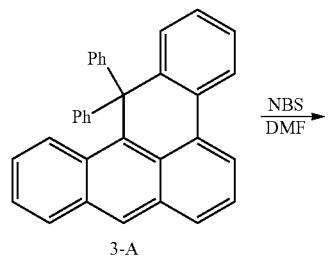

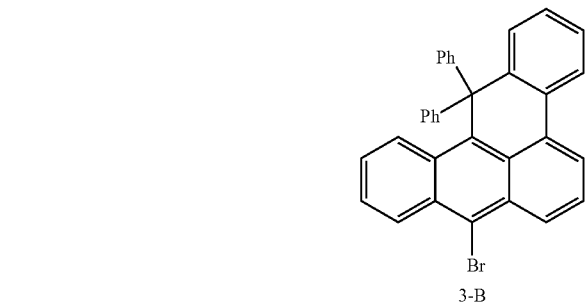

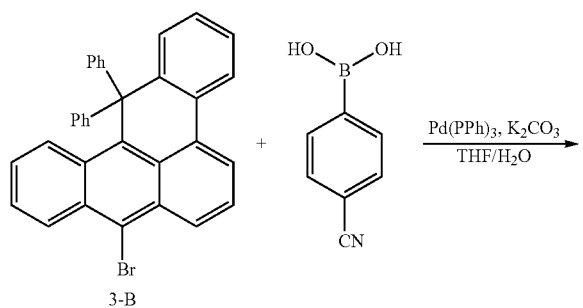

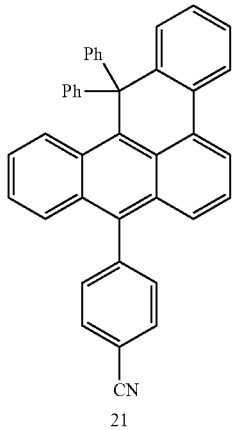

After 1-A (3.26 g, 10 mmol) obtained in the synthesis of Compound 1 was dissolved in 20 ml of THF, 1.4 M methyl magnesium bromide (21.42 ml, 30 mmol) was slowly added dropwise thereto at room temperature. After the reaction was complete, 100 ml of water and 100 ml of ethyl acetate were each added to the result for washing, and the organic layer was collected and dried with anhydrous magnesium sulfate. Solids obtained by concentrating the organic layer under vacuum were dissolved in 25 ml of $CH_2Cl_2$, and then 0.9 ml of $BF_3$ was added thereto and the result was stirred for 30 minutes. After 2 ml of methanol was added thereto to complete the reaction, 200 ml of $CH_2Cl_2$ and 200 ml of water were each added to the result for washing, and only the organic layer was collected and dried with anhydrous magnesium sulfate. The result was concentrated under vacuum, column purified and dried, and as a result, 2.13 g of 3-A was prepared.

3-A (2.13 g, 5.09 mmol), NBS (0.99 g, 5.60 mmol) and 30 ml of DMF were stirred for 1 hour at 0° C. After the reaction was complete, the solution was concentrated under vacuum, the result was washed with 50 ml of an aqueous $Na_2S_2O_3$ solution and 100 ml of $CHCl_3$, and only the organic layer was collected and dried with anhydrous magnesium sulfate. The result was concentrated under vacuum, column purified and dried, and as a result, 2.10 g of 3-B was prepared.

3-B (2.10 g, 4.23 mmol) and (4-cyanophenyl)boronic acid (0.62 g, 4.23 mmol) were dissolved in 20 ml of THF. A solution dissolving $K_2CO_3$ (1.75 g, 12.69 mmol) in 10 ml of water was mixed thereto, and the result was stirred while raising a temperature. When the result started to reflux, tetrakis(triphenylphosphine)palladium (0.15 g, 0.13 mmol) was introduced thereto, and the result was reacted for 15 hours. After cooling the result, the water and the organic layer were separated, and only the organic layer was collected, dried with anhydrous magnesium sulfate, and celite filtered. The result was concentrated under vacuum, column purified and dried, and as a result, 1.82 g of Compound 21 was prepared.

MS[M+H]$^+$=520

PREPARATION EXAMPLE 9

Synthesis of Compound 27

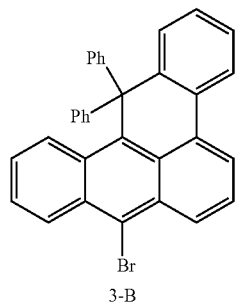

3-B

+

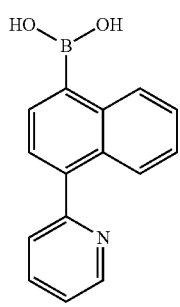

Pd(PPh₃)₃, K₂CO₃
———————→
THF/H₂O

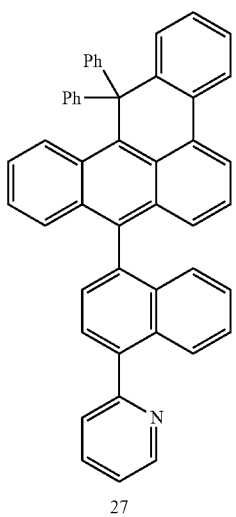

27

4.66 g of Compound 27 was prepared by being reacted and purified in the same manner as in the synthesis of Compound 21, except that 3-B (4.96 g, 10 mmol) obtained in the synthesis process of Compound 21 and (4-(pyridin-2-yl)naphthalen-1-yl)boronic acid (2.49 g, 10 mmol) were used. MS[M+H]⁺=622

PREPARATION EXAMPLE 10

Synthesis of Compound 30

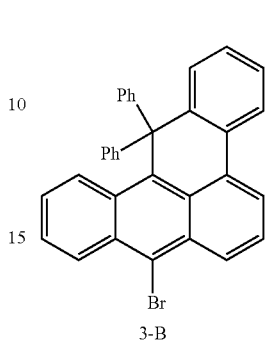

3-B

+

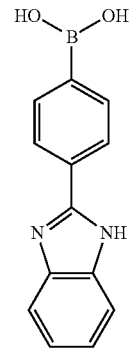

Pd(PPh₃)₃, K₂CO₃
———————→
THF/H₂O

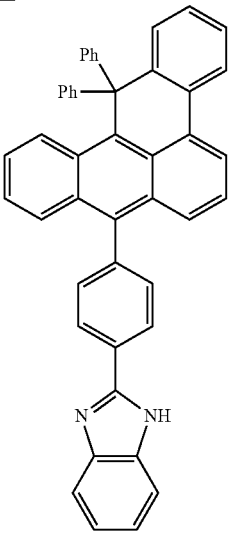

30

4.45 g of Compound 30 was prepared by being reacted and purified in the same manner as in the synthesis of Compound 21, except that 3-B (4.96 g, 10 mmol) obtained in the synthesis process of Compound 21 and (4-(1H-benzo[d]imidazol-2-yl)phenyl)boronic acid (2.38 g, 10 mmol) were used.
MS[M+H]⁺=611

PREPARATION EXAMPLE 11

Synthesis of Compound 33

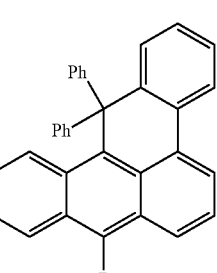

3-B

+

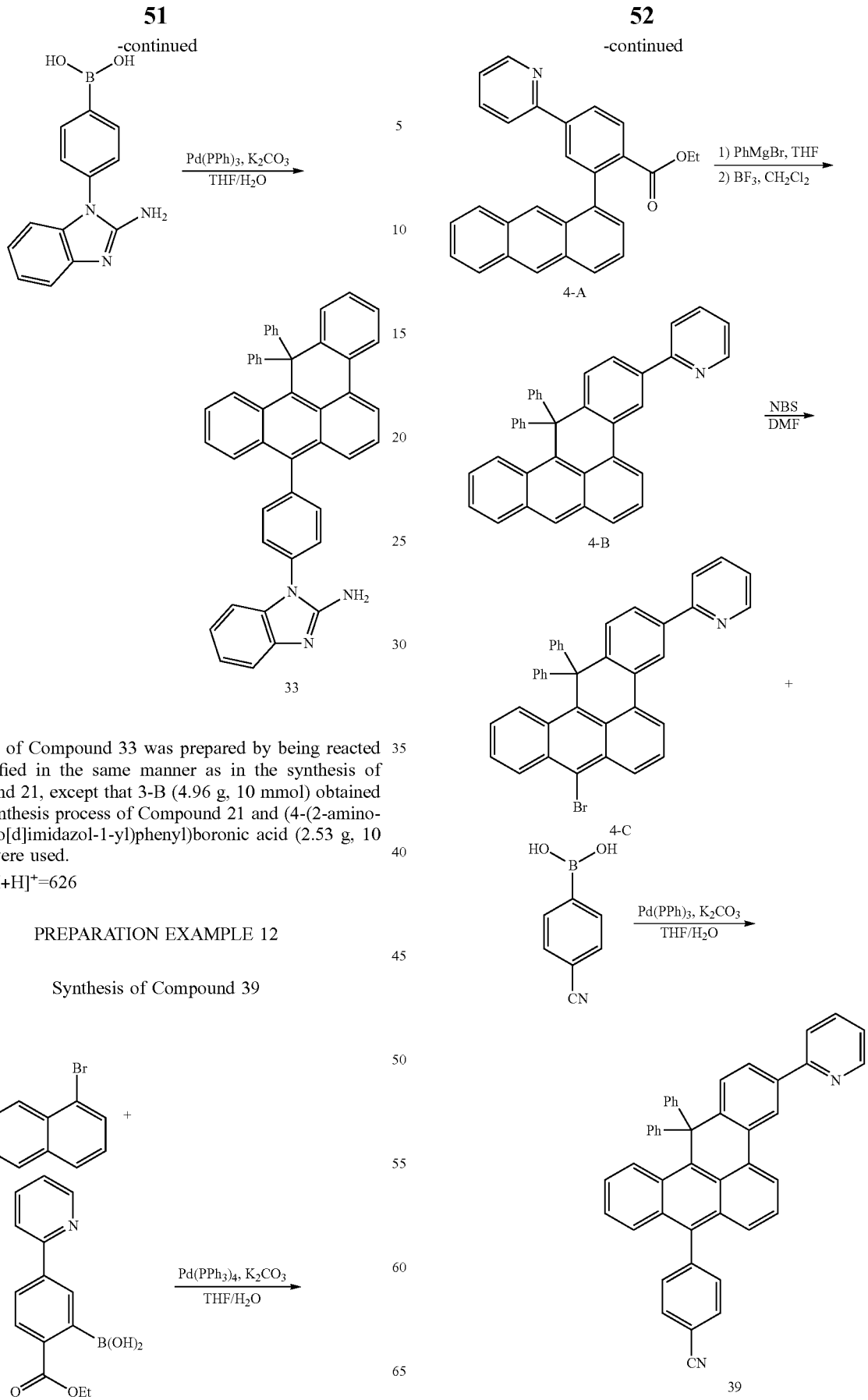
4.88 g of Compound 33 was prepared by being reacted and purified in the same manner as in the synthesis of Compound 21, except that 3-B (4.96 g, 10 mmol) obtained in the synthesis process of Compound 21 and (4-(2-amino-1H-benzo[d]imidazol-1-yl)phenyl)boronic acid (2.53 g, 10 mmol) were used.
MS[M+H]$^+$=626
PREPARATION EXAMPLE 12
Synthesis of Compound 39

After 1-bromoanthracene (2.56 g, 10 mmol) and (2-(ethoxycarbonyl)-5-(pyridin-2-yl)phenyl)boronic acid (2.71 g, mmol) were dissolved in 30 ml of THF, a solution dissolving $K_2CO_3$ (4.15 g, 30 mmol) in 10 ml of water was mixed thereto, and the result was stirred while raising a temperature. When the result started to reflux, tetrakis(triphenylphosphine)palladium (0.35 g, 0.3 mmol) was introduced thereto all at once, and the result was reacted for 16 hours. After the reaction was complete, the result was cooled, the water and the organic layer were separated, and only the organic layer was collected, dried with anhydrous magnesium sulfate, and celite filtered. The result was concentrated under vacuum, column purified and dried, and as a result, 3.06 g of 4-A was prepared.

After 4-A (3.06 g, 7.59 mmol) was dissolved in 20 ml of THF, 1.4 M methyl magnesium bromide (16.26 ml, 22.77 mmol) was slowly added dropwise thereto at room temperature. After the reaction was complete, 100 ml of water and 100 ml of ethyl acetate were each added to the result for washing, and the organic layer was collected and dried with anhydrous magnesium sulfate. Solids obtained by concentrating the organic layer under vacuum were dissolved in 25 ml of $CH_2Cl_2$, and then 0.8 ml of $BF_3$ was added thereto and the result was stirred for 30 minutes. After 2 ml of methanol was added thereto to complete the reaction, 200 ml of $CH_2Cl_2$ and 200 ml of water were each added to the result for washing, and only the organic layer was collected and dried with anhydrous magnesium sulfate. The result was concentrated under vacuum, column purified and dried, and as a result, 1.95 g of 4-B was prepared.

4-B (1.95 g, 3.94 mmol), NBS (0.77 g, 4.33 mmol) and 30 ml of DMF were stirred for 1 hour at 0° C. After the reaction was complete, the solution as concentrated under vacuum, the result was washed with 50 ml of an aqueous $Na_2S_2O_3$ solution and 100 ml of $CHCl_3$, and only the organic layer was collected and dried with anhydrous magnesium sulfate. The result was concentrated under vacuum, column purified and dried, and as a result, 1.85 g of 4-C was prepared.

4-C (1.85 g, 3.23 mmol) and (4-cyanophenyl)boronic acid (0.47 g, 3.23 mmol) were dissolved in 20 ml of THF. A solution dissolving $K_2CO_3$ (1.34 g, 9.69 mmol) in 10 ml of water was mixed thereto, and the result was stirred while raising a temperature. When the result started to reflux, tetrakis(triphenylphosphine)palladium (0.12 g, 0.10 mmol) was introduced thereto, and the result was reacted for 20 hours. After cooling the result, the water and the organic layer were separated, and only the organic layer was collected, dried with anhydrous magnesium sulfate, and celite filtered. The result was concentrated under vacuum, column purified and dried, and as a result, 1.52 g of Compound 39 was prepared.

$MS[M+H]^+=597$

EXAMPLE 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following Chemical Formula to a thickness of 500 Å.

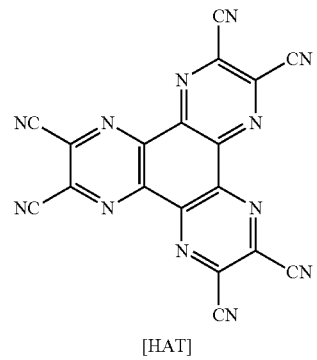

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

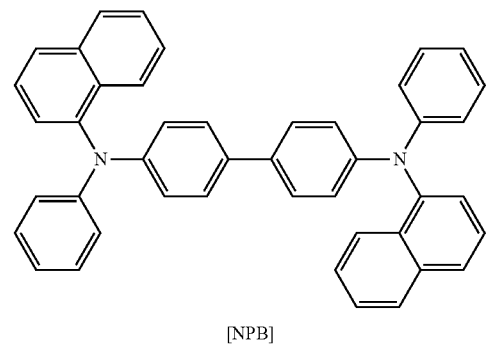

[NPB]

Subsequently, an electron blocking layer was formed on the hole transfer layer to a film thickness of 100 Å by vacuum depositing the following compound N-([1,1'-biphenyl]-4-yl)-N-(4-(11-([1,1'-biphenyl]-4-yl)-11H-benzo[a]carbazol-5-yl)phenyl)-[1,1'-biphenyl]-4-amine (100 Å).

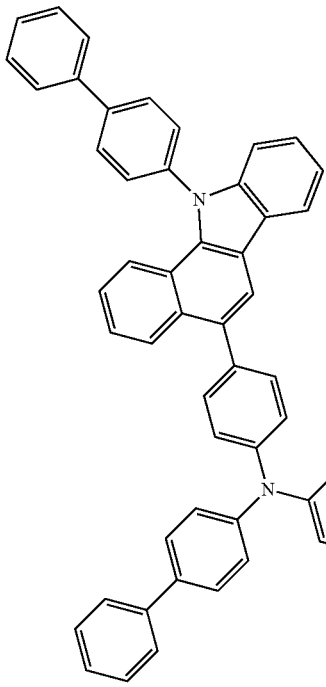

[EB1]

Next, a light emitting layer was formed on the electron blocking layer to a film thickness of 300 Å by vacuum depositing BH and BD as below in a weight ratio of 25:1.

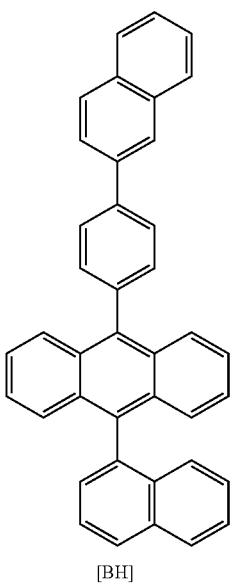

[BH]

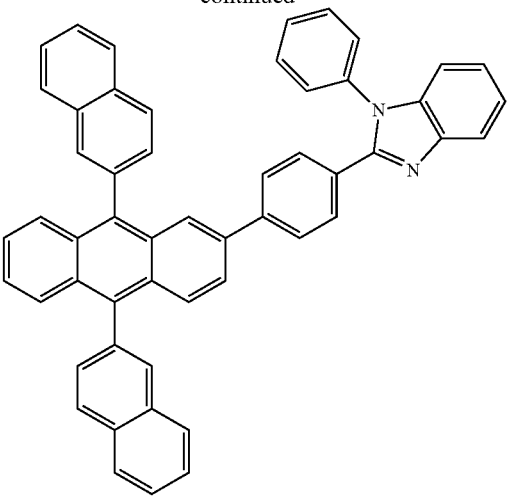

[BD]

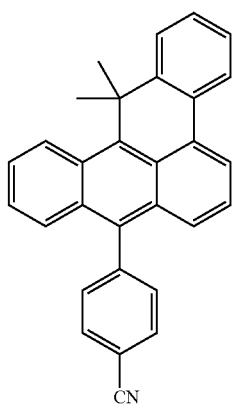

[Compound 1]

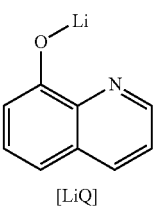

[LiQ]

An electron injection and transfer layer was formed on the light emitting layer to a thickness of 300 Å by vacuum depositing Compound 1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

In the above-mentioned process, the deposition rates of the organic materials were maintained at 0.4 to 0.7 Å/sec, the deposition rates of the lithium fluoride and the aluminum of the cathode were maintained at 0.3 Å/sec and 2 Å/sec, respectively, and the degree of vacuum when being deposited was maintained at $2 \times 10^7$ to $5 \times 10^{-8}$ torr.

EXAMPLE 1-2

An organic light emitting device was manufactured in the same manner as in Example 1-1 except that Compound 7 was used instead of Compound 1.

EXAMPLE 1-3

An organic light emitting device was manufactured in the same manner as in Example 1-1 except that Compound 11 was used instead of Compound 1.

EXAMPLE 1-4

An organic light emitting device was manufactured in the same manner as in Example 1-1 except that Compound 13 was used instead of Compound 1.

EXAMPLE 1-5

An organic light emitting device was manufactured in the same manner as in Example 1-1 except that Compound 14 was used instead of Compound 1.

EXAMPLE 1-6

An organic light emitting device was manufactured in the same manner as in Example 1-1 except that Compound 17 was used instead of Compound 1.

EXAMPLE 1-7

An organic light emitting device was manufactured in the same manner as in Example 1-1 except that Compound 21 was used instead of Compound 1.

EXAMPLE 1-8

An organic light emitting device was manufactured in the same manner as in Example 1-1 except that Compound 27 was used instead of Compound 1.

EXAMPLE 1-9

An organic light emitting device was manufactured in the same manner as in Example 1-1 except that Compound 30 was used instead of Compound 1.

EXAMPLE 1-10

An organic light emitting device was manufactured in the same manner as in Example 1-1 except that Compound 33 was used instead of Compound 1.

EXAMPLE 1-11

An organic light emitting device was manufactured in the same manner as in Example 1-1 except that Compound 39 was used instead of Compound 1.

COMPARATIVE EXAMPLE 1-1

An organic light emitting device was manufactured in the same manner as in Example 1-1 except that the following compound ET 1 was used instead of Compound 1.

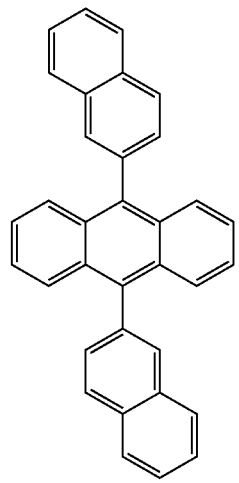

[ET 1]

COMPARATIVE EXAMPLE 1-2

An organic light emitting device was manufactured in the same manner as in Example 1-1 except that the following compound ET 2 was used instead of Compound 1.

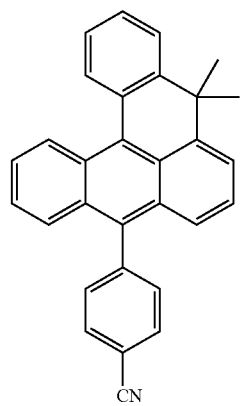

[ET 2]

COMPARATIVE EXAMPLE 1-3

An organic light emitting device was manufactured in the same manner as in Example 1-1 except that the following compound ET 3 was used instead of Compound 1.

[ET 3]

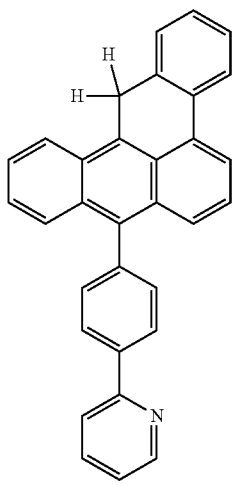

When a current was applied to the organic light emitting devices manufactured in Examples 1-1 to 1-11, and Comparative Examples 1-1 to 1-3, results of Table 1 were obtained.

TABLE 1

| | Compound (Electron Transfer Layer) | Voltage (V@10 mA/cm$^2$) | Efficiency (cd/A@10 mA/cm$^2$) | Color Coordinates (x, y) |
|---|---|---|---|---|
| Example 1-1 | Compound 1 | 4.55 | 6.13 | (0.139, 0.122) |
| Example 1-2 | Compound 7 | 4.52 | 6.18 | (0.138, 0.126) |
| Example 1-3 | Compound 11 | 4.57 | 6.17 | (0.138, 0.127) |
| Example 1-4 | Compound 13 | 4.58 | 6.16 | (0.137, 0.125) |
| Example 1-5 | Compound 14 | 4.63 | 6.00 | (0.136, 0.125) |
| Example 1-6 | Compound 17 | 4.54 | 6.12 | (0.138, 0.127) |
| Example 1-7 | Compound 21 | 4.40 | 6.21 | (0.136, 0.122) |
| Example 1-8 | Compound 27 | 4.45 | 6.24 | (0.137, 0.123) |
| Example 1-9 | Compound 30 | 4.43 | 6.26 | (0.138, 0.125) |
| Example 1-10 | Compound 33 | 4.49 | 6.21 | (0.136, 0.125) |
| Example 1-11 | Compound 39 | 4.54 | 6.15 | (0.136, 0.124) |
| Comparative Example 1-1 | ET 1 | 4.95 | 5.77 | (0.137, 0.125) |
| Comparative Example 1-2 | ET 2 | 4.92 | 5.85 | (0.136, 0.122) |
| Comparative Example 1-3 | ET 3 | 5.01 | 5.80 | (0.139, 0.127) |

As shown in Table 1, when the organic light emitting devices of Examples 1-1 to 1-11 manufactured using fused polycyclic compounds of Chemical Formula 1 including anthracene or phenanthrene as an electron transfer layer were compared to the organic light emitting devices of Comparative Examples 1-1 to 1-3 manufactured using existing materials ETs 1 to 3 as an electron transfer layer, it was identified that the compounds of the present invention exhibited superior properties in terms of efficiency, driving voltage and/or stability of an organic light emitting device since the compounds of the present invention more effectively performed a role of electron transfer.

Compounds described in the present specification can be used as a material of an organic material layer of an organic light emitting device. Compounds according to at least one embodiment of the present specification are capable of efficiency enhancement, low driving voltage and/or lifespan property enhancement in an organic light emitting device. In particular, compounds described in the present specification can be used as an electron transfer material.

Compounds according to at least one embodiment of the present specification have high melting points and $T_g$s, and therefore, mixing with adjacent organic thin film layers or crystallization does not occur even when the compounds are exposed to heat generated when manufacturing a device or heat generated from driving. Due to bulky substituents substituting anthracene surroundings, a three-dimensional property is obtained when laminating this molecule in a direction perpendicular to the molecular plane. As a result, crystallization becomes more difficult, and films are readily formed.

Compounds according to at least one embodiment of the present specification have high quantum efficiency, power efficiency and/or chemical stability in an organic light emitting device. Compounds according to at least one embodiment of the present specification are capable of increasing luminance, purity and/or a lifespan in an organic light emitting device.

What is claimed is:
1. A compound represented by the following Chemical Formula 2:

[Chemical Formula 2]

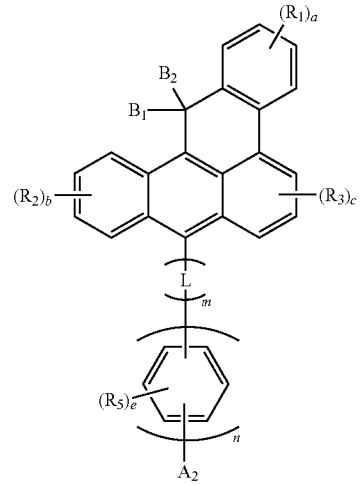

wherein, in Chemical Formula 2, $R_1$ to $R_3$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, $R_5$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heterating, $B_1$ and $B_2$ are the same as or different from each other, and each independently a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, $A_2$ is a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bonds to adjacent substituents to form a substituted or unsubstituted hydrocarbon ring or heterating, L is a direct bond; a substituted or unsubstituted arylene group; or a substituted or unsubstituted heteroarylene group, m is an integer of 0 to 5, n is an integer of 0 or 1, a, b, and e are the same as or different from each other, and each independently an integer of 0 to 4, c is an integer of 0 to 3, when a is two or greater, $R_1$s are the same as or different from each other, when b is two or greater, $R_2$s are the same as or different from each other, when c is two or greater, $R_3$s are the same as or different from each other, when e is two or greater, $R_5$s are the same as or different from each other, and when m is two or greater, Ls are the same as or different from each other.

2. The compound of claim 1, wherein Chemical Formula 2 is represented by the following Chemical Formula 3:

[Chemical Formula 3]

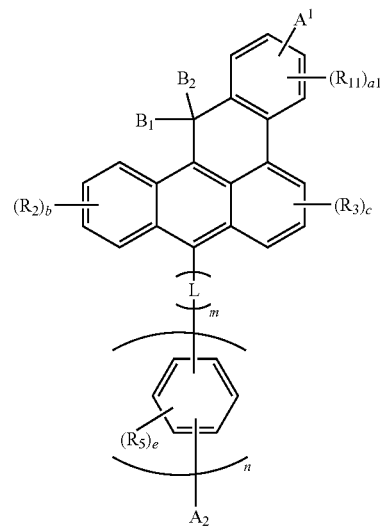

wherein, in Chemical Formula 3, definitions of $B_1$, $B_2$, L, m, $R_2$, $R_3$, $R_5$, $A_2$, n, e, b and c are the same as in Chemical Formula 2;

$A_1$ is hydrogen; a nitrile group; a nitro group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group, $R_{11}$ is hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, a1 is an integer of 0 to 3, and when a1 is two or greater, $R_{11}$s are the same as or different from each other.

3. The compound of claim 2, wherein $A_1$ in Chemical Formula 3 is hydrogen; a nitrile group; a substituted or unsubstituted pyridyl group; or a substituted or unsubstituted benzimidazole group, and $A_2$ is a nitrile group; a substituted or unsubstituted pyridyl group; a substituted or unsubstituted benzimidazole group; or a substituted or unsubstituted benzoimidazophenanthridine group.

4. The compound of claim 2, wherein $A_1$ in chemical Formula 3 is hydrogen or selected from among the following structures, and $A_2$ in Chemical Formula 3 is selected from among the following structures:

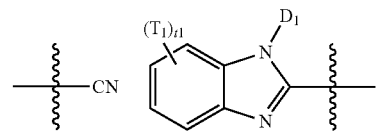

-continued

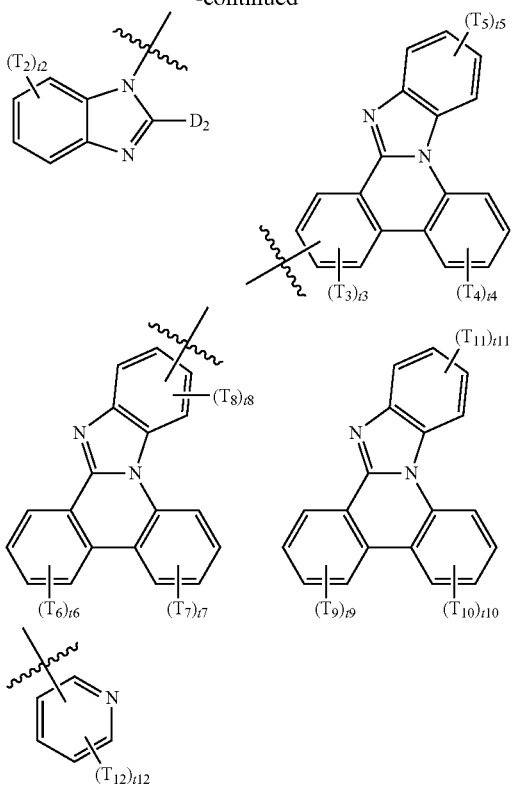

wherein, in the structures,
T₁ to T₁₂ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring,
D₁ and D₂ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring,
t1, t2, t4, t5, t6, t7, t9, t11 and t12 are the same as or different from each other, and each independently an integer of 0 to 4, t3, t8 and t10 are the same as or different from each other, and each independently an integer of 0 to 3,
when t1 is two or greater, T₁s are the same as or different from each other,
when t2 is two or greater, T₂s are the same as or different from each other,
when t3 is two or greater, T₃s are the same as or different from each other,
when t4 is two or greater, T₄s are the same as or different from each other,
when t5 is two or greater, T₅s are the same as or different from each other,
when t6 is two or greater, T₆s are the same as or different from each other,
when t7 is two or greater, T₇s are the same as or different from each other,
when t8 is two or greater, T₈s are the same as or different from each other,
when t9 is two or greater, T₉s are the same as or different from each other,
when t10 is two or greater, T₁₀s are the same as or different from each other,
when t11 is two or greater, T₁₁s are the same as or different from each other, and
when t12 is two or greater, T₁₂s are the same as or different from each other.

5. The compound of claim 1, wherein L in Chemical Formula 2 is selected from among the following structures:

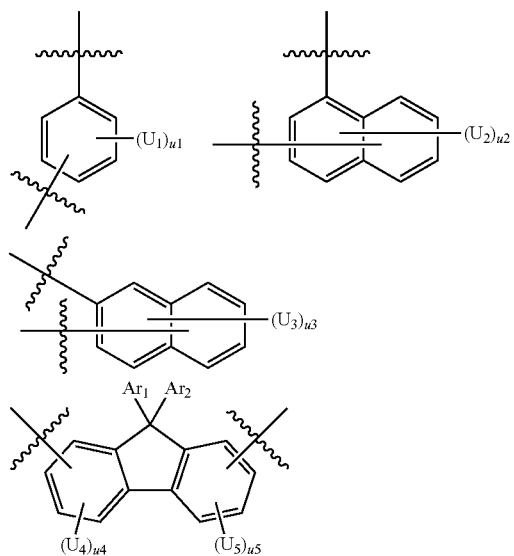

wherein, in the structures,
U₁ to U₅ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $Ar_1$ and $Ar_2$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, u1 is an integer of 0 to 4, u2 and u3 are the same as or different from each other, and each independently an integer of 0 to 6, u4 and u5 are the same as or different from each other, and each independently an integer of 0 to 3, when u1 is two or greater, $U_1$s are the same as or different from each other, when u2 is two or greater, $U_2$s are the same as or different from each other, when u3 is two or greater, $U_3$s are the same as or different from each other, when u4 is two or greater, $U_4$s are the same as or different from each other, and when u5 is two or greater, $U_5$s are the same as or different from each other.

6. The compound of claim 1, wherein Chemical Formula 2 is represented by the following Chemical Formula 4 or 5:

[Chemical Formula 4]

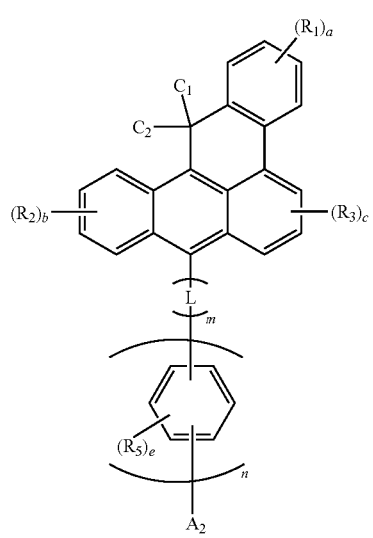

-continued

[Chemical Formula 5]

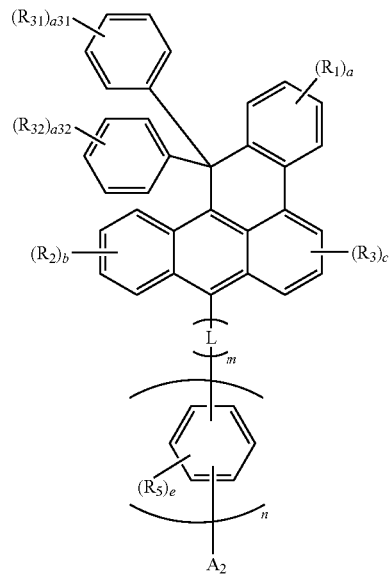

wherein, in Chemical Formulae 4 and 5, definitions of L, m, $R_1$ to $R_3$, $R_5$, $A_2$, n, e, a, b and c are the same as in Chemical Formula 2, $R_{31}$ and $R_{32}$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, $C_1$ and $C_2$ are the same as or different from each other, and each independently a substituted or unsubstituted alkyl group, a31 and a32 are the same as or different from each other, and each independently an integer of 0 to 5, when a31 is two or greater, $R_{31}$s are the same as or different from each other, and when a32 is two or greater, $R_{32}$s are the same as or different from each other.

7. The compound of claim 1, wherein Chemical Formula 2 is represented by any one of the following Chemical Formulae 6 to 9:

[Chemical Formula 6]

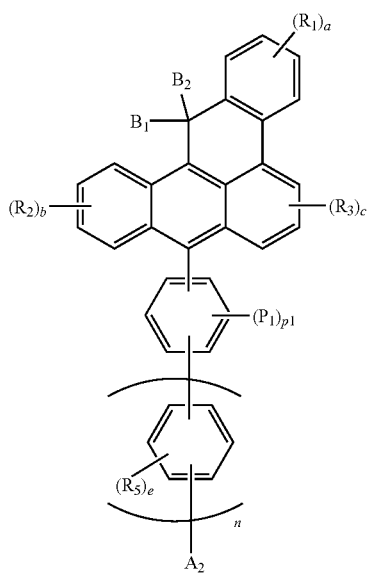

[Chemical Formula 7]

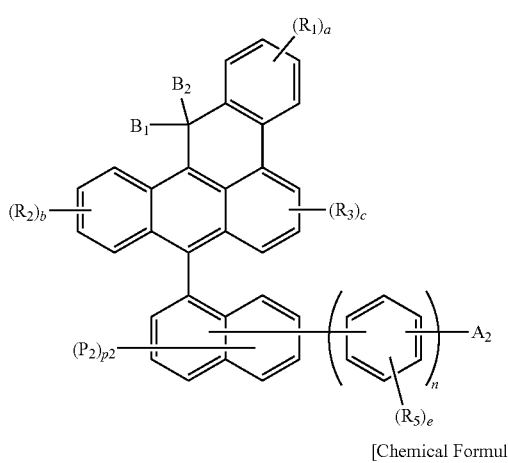

[Chemical Formula 8]

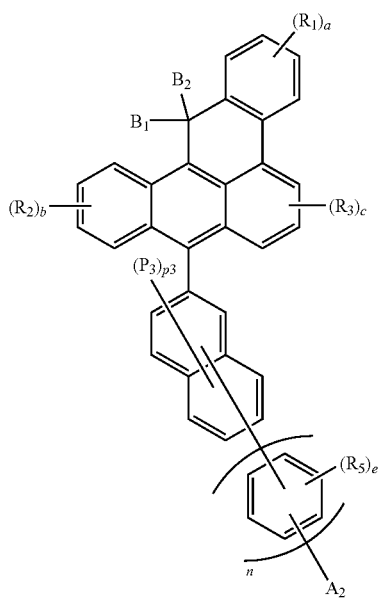

[Chemical Formula 9]

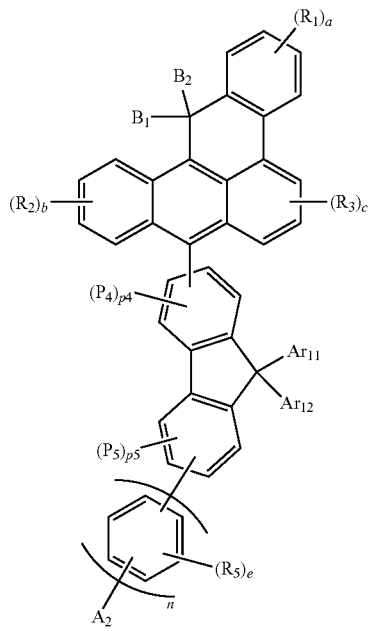

wherein, in Chemical Formulae 6 to 9, definitions of $B_1$, $B_2$, $R_1$ to $R_3$, $R_5$, $A_2$, n and e, a, b and c are the same as in Chemical Formula 2, $Ar_{11}$ and $Ar_{12}$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, $P_1$ to $P_5$ are the same as or different from each other, and each independently hydrogen; deuterium; a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or heteroring, p1 is an integer of 0 to 4, p2 and p3 are the same as or different from each other, and each independently an integer of 0 to 6, p4 and p5 are the same as or different from each other, and each independently an integer of 0 to 3, when p1 is two or greater, $P_1$s are the same as or different from each other, when p2 is two or greater, $P_2$s are the same as or different from each other, when p3 is two or greater, $P_3$s are the same as or different from each other, when p4 is two or greater, $P_4$s are the same as or different from each other, and when p5 is two or greater, $P_5$s are the same as or different from each other.

8. The compound of claim 1, wherein the compound of Chemical Formula 2 is selected from among the following structures;

1

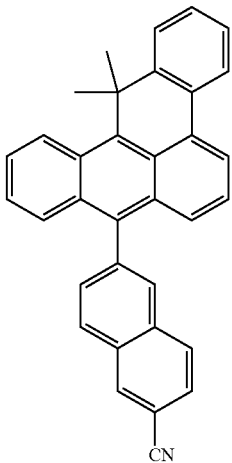

2

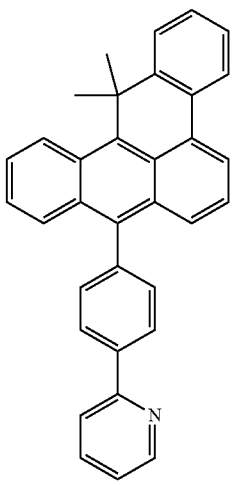

3

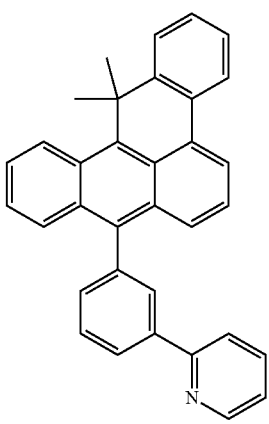

4

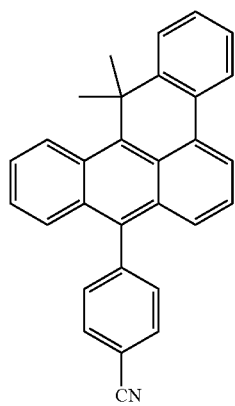

5

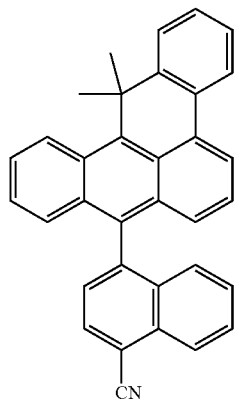

6

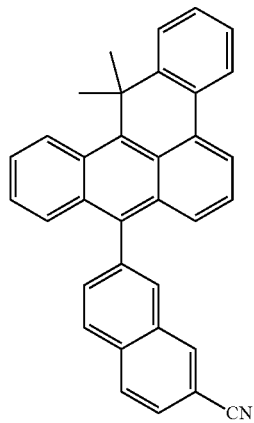

71
-continued
7
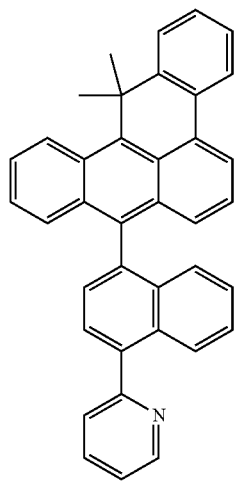
8
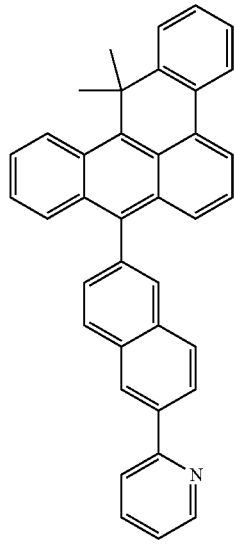
9
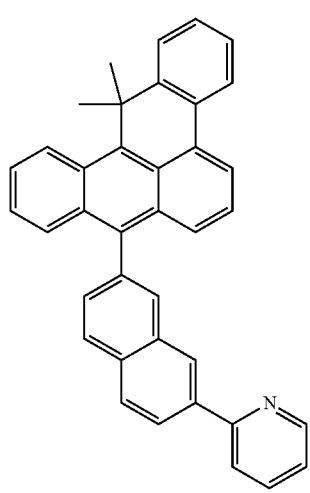
72
-continued
10
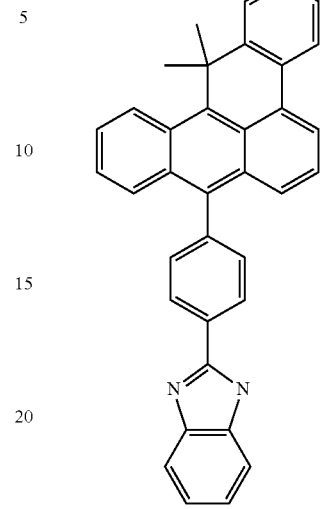
11
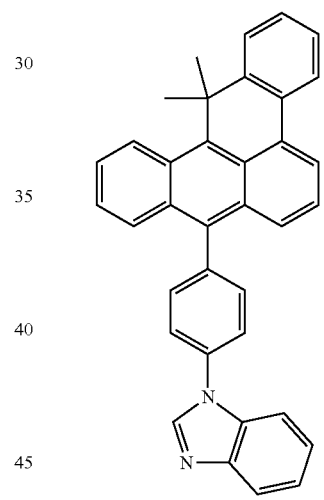
12
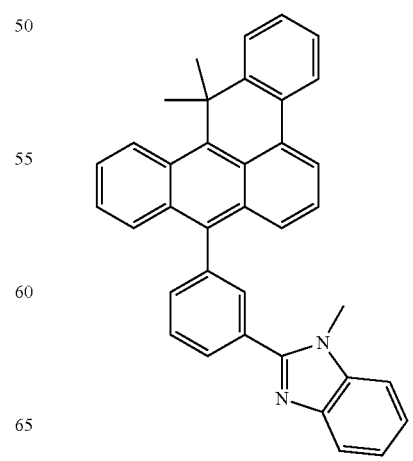

73
-continued
13
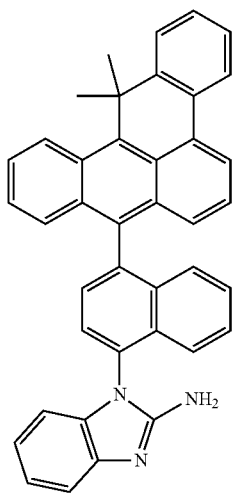
14
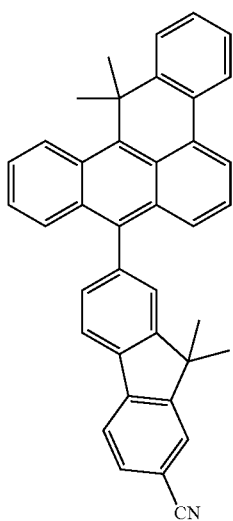
15
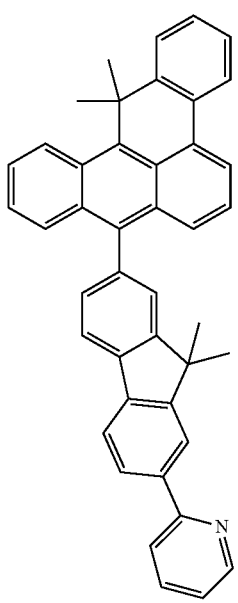
74
-continued
16
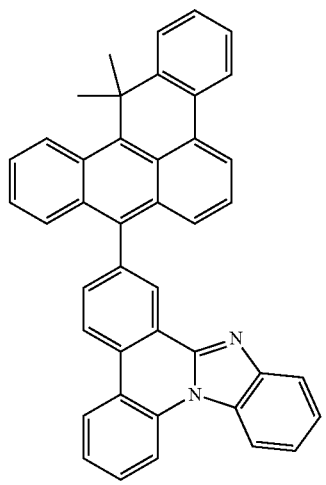
17
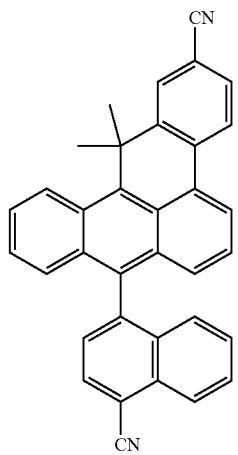
18
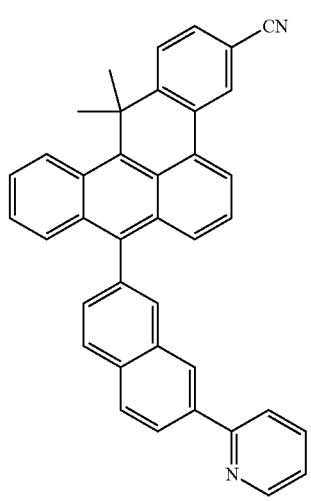

-continued
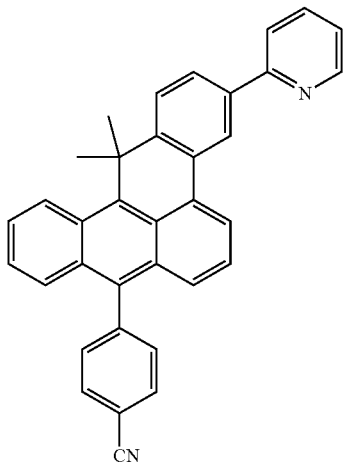
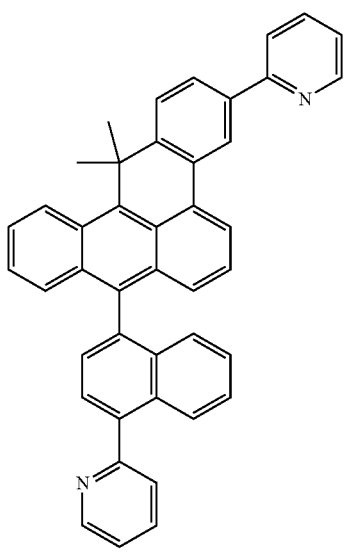
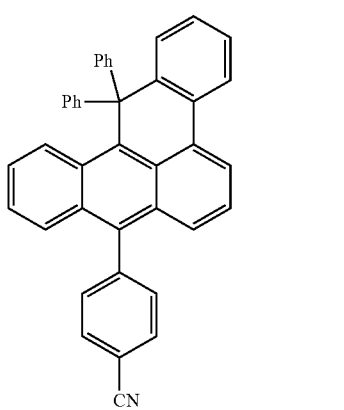
-continued
19
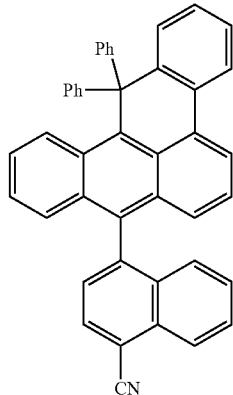
20
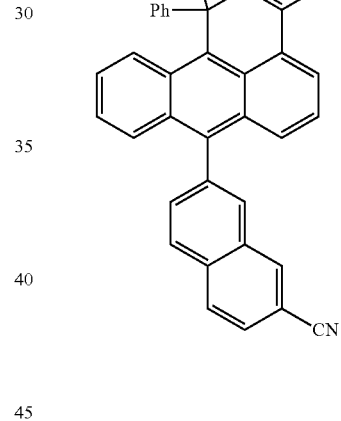
21
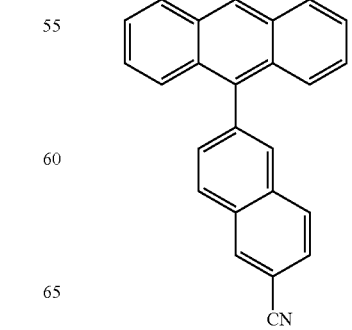
22
23
24

77
-continued
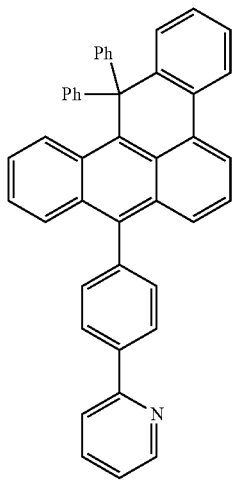
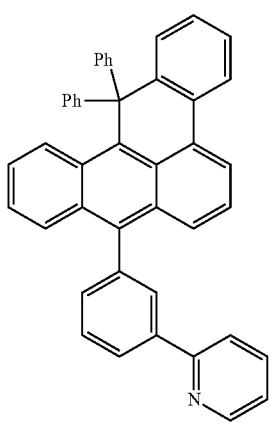
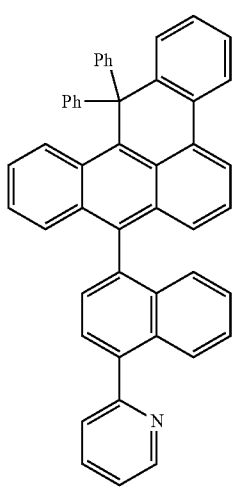
78
-continued
25
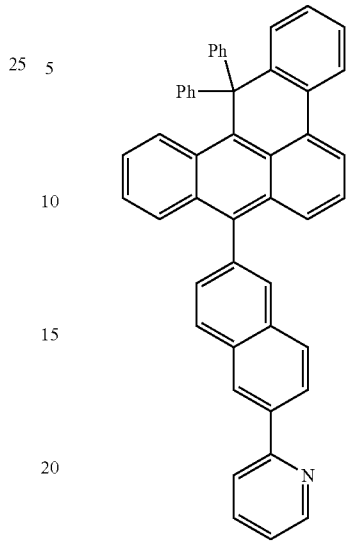
26
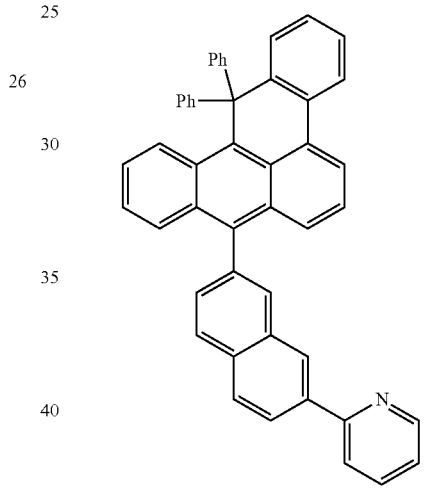
27
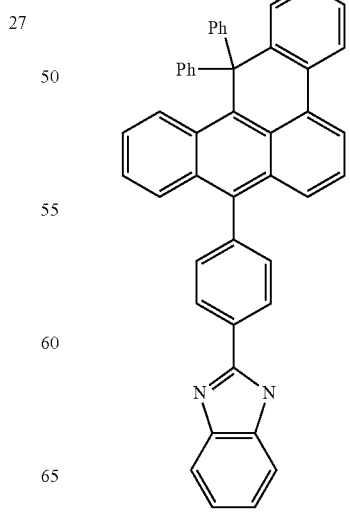

31
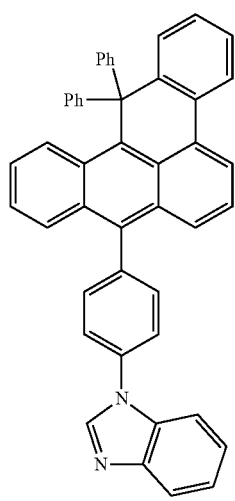
32
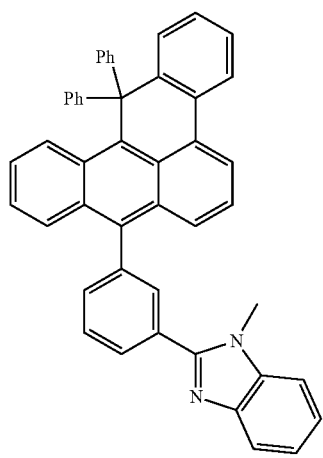
33
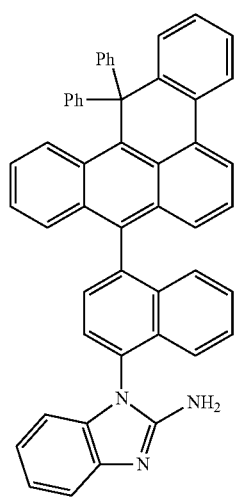
34
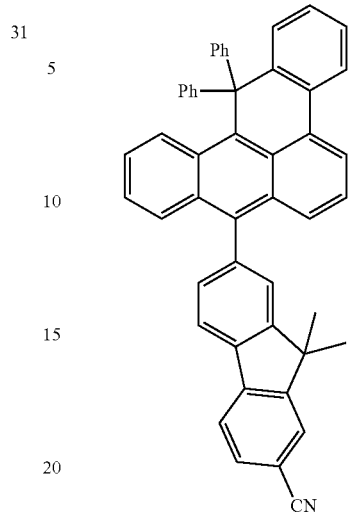
35
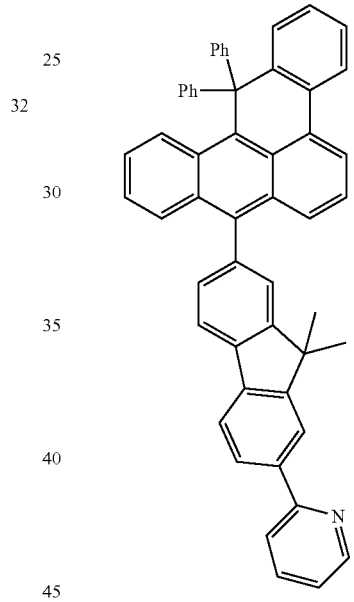
36
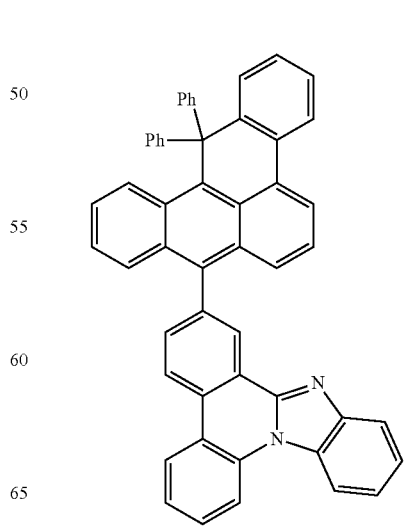

-continued

37 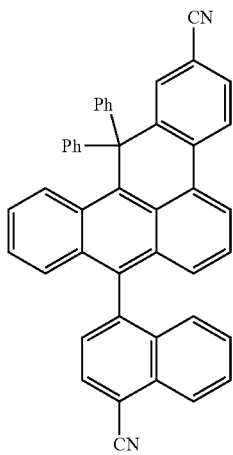

38 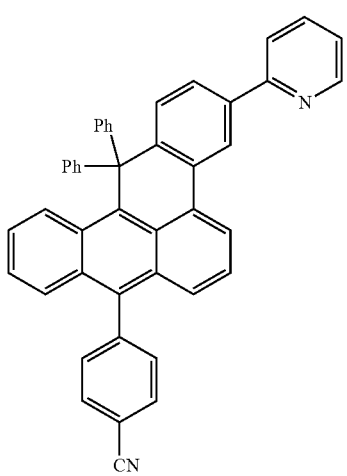

39

-continued

40 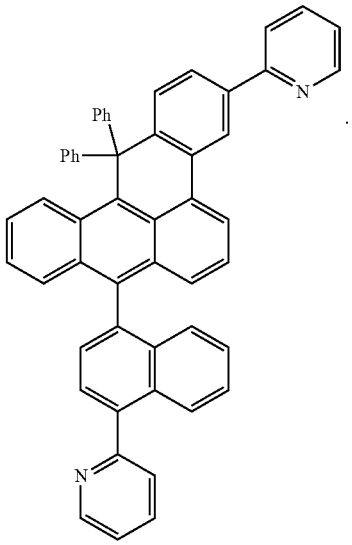

9. An organic light emitting device comprising:
a first electrode;
a second electrode provided opposite to the first electrode; and
one or more organic material layers provided between the first electrode and the second electrode,
wherein one or more layers of the organic material layers include the compound represented by the following Chemical Formula 1:

[Chemical Formula 1]

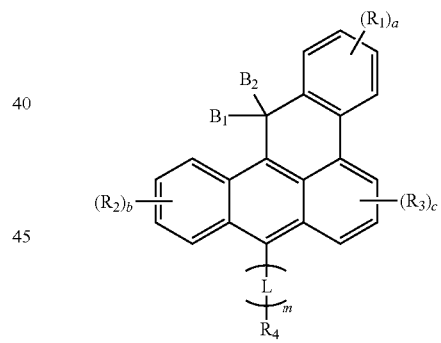

wherein, in Chemical Formula 1,
$R_1$ to $R_4$ are the same as or different from each other, and each independently hydrogen; deuterium a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or adjacent two or more substituents bond to each other to form a substituted or unsubstituted hydrocarbon ring or a substituted or unsubstituted heteroring, B$_1$ and B$_2$ are the same as or different from each other, and each independently a halogen group; a nitrile group; a nitro group; an amino group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted aralkyl group; a substituted or unsubstituted aralkenyl group; a substituted or unsubstituted alkylaryl group; a substituted or unsubstituted alkylamine group; a substituted or unsubstituted heteroarylamine group; or a substituted or unsubstituted arylamine group, or bond to each other to form a substituted or unsubstituted ring, L is a direct bond; a substituted or unsubstituted arylene group; or a substituted or unsubstituted heteroarylene group, m is an integer of 0 to 5, a and b are the same as or different from each other, and each independently an integer of 0 to 4, c is an integer of 0 to 3, when a is two or greater, R$_1$s are the same as or different from each other, when b is two or greater, R$_2$s are the same as or different from each other, when c is two or greater, R$_3$s are the same as or different from each other, and when m is two or greater, Ls are the same as or different from each other.

10. The organic light emitting device of claim 9, wherein the organic material layer including the compound is an electron transfer layer.

\* \* \* \* \*